US012788772B2

(12) United States Patent
Hobman et al.

(10) Patent No.: US 12,788,772 B2
(45) Date of Patent: Nov. 10, 2026

(54) USE OF WNT/BETA-CATENIN PATHWAY INHIBITORS TO BLOCK REPLICATION OF SARS-CoV-2 AND OTHER PATHOGENIC VIRUSES

(71) Applicant: THE GOVERNORS OF THE UNIVERSITY OF ALBERTA, Edmonton (CA)

(72) Inventors: Thomas Hobman, Edmonton (CA); Zaikun Xu, Edmonton (CA); Cheung Pang Wong, Edmonton (CA)

(73) Assignee: THE GOVERNORS OF THE UNIVERSITY OF ALBERTA, Edmonton (CA)

( * ) Notice: Subject to any disclaimer, the term of this patent is extended or adjusted under 35 U.S.C. 154(b) by 639 days.

(21) Appl. No.: 18/018,782

(22) PCT Filed: Jul. 30, 2021

(86) PCT No.: PCT/CA2021/051077
§ 371 (c)(1),
(2) Date: Jan. 30, 2023

(87) PCT Pub. No.: WO2022/020967
PCT Pub. Date: Feb. 3, 2022

(65) Prior Publication Data
US 2023/0293565 A1 Sep. 21, 2023

Related U.S. Application Data

(60) Provisional application No. 63/083,533, filed on Sep. 25, 2020, provisional application No. 63/059,390, filed on Jul. 31, 2020.

(51) Int. Cl.
*A61K 31/7068* (2006.01)
*A61K 31/4468* (2006.01)

(52) U.S. Cl.
CPC ...... *A61K 31/7068* (2013.01); *A61K 31/4468* (2013.01)

(58) Field of Classification Search
None
See application file for complete search history.

(56) References Cited

U.S. PATENT DOCUMENTS

2020/0017857 A1 1/2020 Monga et al.

FOREIGN PATENT DOCUMENTS

| | | | |
|---|---|---|---|
| EP | 4112049 | A1 | 1/2023 |
| WO | WO-2015/134525 | A1 | 9/2015 |
| WO | WO-2018045182 | A1 | 3/2018 |

OTHER PUBLICATIONS

Ge Y, Tian T, Huang S, Wan F, Li J, Li S, Yang H, Hong L, Wu N, Yuan E, Cheng L. A data-driven drug repositioning framework discovered a potential therapeutic agent targeting COVID-19. BioRxiv. Mar. 12, 2020:Mar. 2020.*
Al-Tawfiq JA, Al-Homoud AH, Memish ZA. Remdesivir as a possible therapeutic option for the COVID-19. Travel medicine and infectious disease. Mar. 5, 2020;34:101615.*
Albrecht et al., "Cell Biology of Canonical Wnt Signaling," Annual Review of Cell and Development Biology, Jul. 2021, vol. 37, pp. 369-389 (23 pages).
Carboni et al., "Can Pioglitazone Be Potentially Useful Therapeutically in Treating Patients With Covid-19?," Medical Hypotheses, Jul. 2020, 140:109776 (5 pages).
Curtin et al., "Repositioning Parp Inhibitors for SARS-CoV-2 Infection(COVID-19); a New Multi-pronged Therapy for Acute Respiratory Distress Syndrome?," British Journal of Pharmacology, Aug. 2020, vol. 177 (16), pp. 3635-3645.
Desmyter et al., Defectiveness of Interferon Production and of Rubella Virus Interference in a Line of African Green Monkey Kidney Cells (Vero), Journal of Virology, 1968, vol. 2 (10), pp. 955-961.
Dixit et al., "Peroxisomes are Signaling Platforms for Antiviral Innate Immunity," Cell, 2010, vol. 141 (4), pp. 668-681.
Fujiki et al., "Recent Insights into Peroxisome Biogenesis and Associated Diseases," Journal of Cell Science, May 2020, vol. 133 (9), pp. 1-9.
International Patent Application No. PCT/CA2021/051077, International Preliminary Report on Patentability, mailed Feb. 9, 2023 (8 pages).
International Patent Application No. PCT/CA2021/051077, International Search Report and Written Opinion mailed Nov. 5, 2021 (13 pages).
Odendall et al., "Diverse Intracellular Pathogens Activate Type III Interferon Expression from Peroxisomes," Nature Immunology, 2014, vol. 15 (8), pp. 717-726 (12 pages).
Wong et al., Interplay between Zika Virus and Peroxisomes During Infection, Cells, 2019, vol. 8 (725), pp. 1-26 (16 pages).
Wong et al., "Targeted Elimination of Peroxisomes During Viral Infection: Lessons from HIV and Other Viruses," DNA and Cell Biology, 2018, vol. 37 (5), pp. 417-421.
Xu et al., "The HIV-1 Accessory Protein Vpu Downregulates Peroxisome Biogenesis," mBio, Mar./Apr. 2020, vol. 11 (2), pp. 1-21.
You et al., "Development of a Triazole Class of Highly Potent Poren Inhibitors," Bioorganic and Medicinal Chemistry Letters, Dec. 2016, vol. 26 (24), pp. 5891-5895.
Zahedipour et al., "Potential Effects of Curcumin in the Treatment of Covid-19 Infection," Phytotherapy Research, Apr. 2020, vol. 34 (11), pp. 2911-2920.
European Patent Application No. 20210849133, Extended European Search Report (EESR) dated Jul. 9, 2024 (15 pages).
Mishra et al., "Curcumin Induces Apoptosis in Pre-B Acute Lymphoblastic Leukemia Cell Lines Via PARP-1 Cleavage", Asian Pac J Cancer Prev. 17(8):3865-9 (Jan. 2016) (5 pages).

* cited by examiner

*Primary Examiner* — Patrick T Lewis
(74) *Attorney, Agent, or Firm* — Clark & Elbing LLP

(57) ABSTRACT

Use of Wnt/Beta-catenin pathway inhibitors to block replication of SARS-CoV-2 and other pathogenic viruses.

11 Claims, 41 Drawing Sheets

Pre-treatment of Calu-3 cells with Wnt inhibitors reduces SARS-CoV-2 in a dose-dependent manne

Wnt inhibitors reduce replication of SARS-CoV-2 in a dose-dependent manner when added to Calu-3 cells post-infection

Wnt inhibitors enhance IFNβ expression in response to Sendai virus infection

Some Wnt inhibitors enhance IFNλ expression in response to Sendai virus infection

Pre-treatment of Vero cells with Wnt inhibitors does not significantly reduce SARS-CoV-2 replication

Pre-treatment of Normal Human Bronchial Epithelial cells with Wnt inhibitors reduces replication of SARS-CoV-2

Fold Induction of IFNB at 16 hr post infection of Sendai virus in A549 cells treated with Wnt inhibitors/PPAR agonists

USE OF WNT/BETA-CATENIN PATHWAY INHIBITORS TO BLOCK REPLICATION OF SARS-CoV-2 AND OTHER PATHOGENIC VIRUSES

CROSS REFERENCE TO RELATED APPLICATIONS

This application claim priority to U.S. provisional patent applications 63/083,533, filed Sep. 25, 2020, and U.S. 63/059,390, filed Jul. 31, 2020, the entire contents of both are hereby incorporated by reference.

FIELD

The present disclosure relates generally to use of Wnt/Beta-catenin pathway inhibitors and other peroxisome inducers to block replication of SARS-CoV-2 and other pathogenic viruses.

BACKGROUND

The International Committee on Taxonomy of Viruses (ICTV) announced "severe acute respiratory syndrome coronavirus 2 (SARS-CoV-2)" as the name of the new virus on 11 Feb. 2020. The World Health Organization (WHO) announced "COVID-19" as the name of the disease associated with this virus. SARS-CoV-2 is responsible for the outbreak of COVID-19.

Globally, to date, more than 195 Million people have been infected with SARS-CoV-2, resulting in more than 4 million deaths.

There remains an urgent need for drugs that prevent infection by SAR-CoV-2.

SUMMARY

In one aspect there is provided a method of treating a subject infected with SARS-CoV-2, suspected of being infected with SARS-CoV-2, or at risk of being infected with SARS-CoV-2, comprising or consisting of, administering a therapeutically effective amount of a Wnt/β-catenin signaling inhibitor.

In one example, said Wnt/β-catenin signaling inhibitor is IWP-O1, IWP-2, IWP-L6, iCRT3, LGK-974, WIK14, Wnt-C59, ICG-001, IWR-1-endo, Silibinin, NCB-0846, KYA1797K, Foxy-5 (Wnt5a mimic peptide), PRI-724, ETC-1922159, PNU-74654, Carnosic acid, Pyrvinium, iCRT-14, Sulindac, SM04755, Famotidine, NSC668036, E7449, Dvl-PDZ Domain Inhibitor II, Olaparib, Niraparib, PJ34 HCl, Capmatinib, Curcumin, or Genistein, triptolide.

In one example, said Wnt/β-catenin signalling inhibitor is Wogonin, Ant1.4Br/Ant1.4Cl, Ipafricept, APCDD1, FzM1, Fz7-21, OTSA101, OTSA101-DTPA-90Y, BNC101, Gigantol, salinomycin, IGFBP-4, DKN-01, Compound 3289-8625, FJ9, NSC668036, peptide Pen-N3, 2X-121, AZ1366, AZ-6102, G007-LK, G244-LM, IWR-1, JW55, JW67, JW74, K-756, MN-64, MSC2504877, NVP-TNKS656, RK-287107, TC-E5001, WIK14, XAV939, TCS 183, 21H7, isoquercitrin, KY1220, MSAB, NRX-252114, BC21, BC2059, CCT031374, CCT036477, CGP049090, CWP232228, ethacrynic acid, FH535, iCRT3, iCRT5, iCRT14, LF3, NLS-StAx-h, PKF115-584, PKF118-310, PKF118-744, PNU-74654, quercetin, ZTM000990, KY-05009, NCB-0846, IQ-1, windorphen, YH249/250, C-82, ICG-001, PRI-724, retinoids, vitamin D3, SAH-BCL9, Adavivint (SM04690, lorecivivint), artesunate, cardamonin, cardionogen, CCT031374, diethyl benzylphosphonate, echinacoside, KY02111, pamidronic acid, or specnuezhenide In one example, further comprising administering Molnupiravir (MK-4482/EIDD-2801 or Remdesivir to said subject.

In one example, said subject is a human.

In one aspect there is provided a method of treating a subject infected with SARS-CoV-2, suspected of being infected with SARS-CoV-2, or at risk of being infected with SARS-CoV-2, comprising or consisting of, administering a therapeutically effective amount of a PARP inhibitor.

In one example, wherein the PPAR inhibitor is E7449, PJ34 HCl, WIK14, Olaparib and Niraparib are PARP or Tankyrase inhibitors.

In one example, wherein the PARP inhibitor is WIK14, E7449, PJ34 HCl, Olaparib, Talazparib, XAV-939, Veliparib, AZD5305, Fluzoparib, Rucaparib, RBN-2397, PJ34, Pamiparib, G007-LK, JW55, BGP-15, NMS-P118, RBN012759, EB-47 dihydrochloride, AZ6102, RK-287107, GeA-69, MN-64, 5,7,4'-Trimthoxyflavone, Oroxin A, NU0125, BYK204165, K-756, 2-Methylquinazolin-4-ol, AZ-9842, OUL35, Mefuparib hydrochloride, Senaparib, Tankyrase-IN-2, PARP-2-IN-1, BR102375, EB-47, 4'-Methoxychalcone, DR2313, 3-Methoxybenzamide, 5,7-Dihydroxychromone, BRCA1-IN-1, or WD2000-012547.

In one aspect there is provided a method of treating a subject infected with SARS-CoV-2, suspected of being infected with SARS-CoV-2, or at risk of being infected with SARS-CoV-2, comprising or consisting of, administering a therapeutically effective amount of a compound or composition that increases the density of peroxisomes in a plurality of cells in the subject.

In one example, wherein said compound or composition that increases the density of peroxisomes in a plurality of cells in the subject is IWP-O1, IWP-2, IWP-L6, iCRT3, LGK-974, WIK14, Wnt-C59, ICG-001, IWR-1-endo, Silibinin, NCB-0846, KYA1797K, Foxy-5 (Wnt5a mimic peptide), PRI-724, ETC-1922159, PNU-74654, Carnosic acid, Pyrvinium, iCRT-14, Sulindac, SM04755, Famotidine, NSC668036, E7449, Dvl-PDZ Domain Inhibitor II, Olaparib, Niraparib, PJ34 HCl, Capmatinib, Curcumin, or Genistein, triptolide.

In one example, wherein said compound or composition that increases the density of peroxisomes in a plurality of cells in the subject is Pyrvinium, KYA1797K, Wnt-C59, ETC-1922159, iCRT-14, SM04755, E7449, IWP-O1, NCB0846, LGK-974, Triptolide or PJ354 HCL.

In one example, wherein said compound or composition that increases the density of peroxisomes in a plurality of cells in the subject is Wogonin, Ant1.4Br/Ant1.4Cl, Ipafricept, APCDD1, FzM1, Fz7-21, OTSA101, OTSA101-DTPA-90Y, BNC101, Gigantol, salinomycin, IGFBP-4, DKN-01, Compound 3289-8625, FJ9, NSC668036, peptide Pen-N3, 2X-121, AZ1366, AZ-6102, G007-LK, G244-LM, IWR-1, JW55, JW67, JW74, K-756, MN-64, MSC2504877, NVP-TNKS656, RK-287107, TC-E5001, WIKI4, XAV939, TCS 183, 21H7, isoquercitrin, KY1220, MSAB, NRX-252114, BC21, BC2059, CCT031374, CCT036477, CGP049090, CWP232228, ethacrynic acid, FH535, iCRT3, iCRT5, iCRT14, LF3, NLS-StAx-h, PKF115-584, PKF118-310, PKF118-744, PNU-74654, quercetin, ZTM000990, KY-05009, NCB-0846, IQ-1, windorphen, YH249/250, C-82, ICG-001, PRI-724, retinoids, vitamin D3, SAH-BCL9, Adavivint (SM04690, lorecivivint), artesunate, cardamonin, cardionogen, CCT031374, diethyl benzylphosphonate, echinacoside, KY02111, pamidronic acid, or specnuezhenide.

In one example, wherein said compound or composition that increases the density of peroxisomes in a plurality of cells in the subject is an inhibitor of Porcupine.

In one example, wherein the Porcupine inhibitor is CGX1321, GNF-6231, IWP-3, IWP-4, IWP-12, IWP-L6, or RXC004.

In one example, wherein said compound or composition that increases the density of peroxisomes in a plurality of cells in the subject is an inhibitor of β-catenin.

In one example, wherein said compound or composition that increases the density of peroxisomes in a plurality of cells in the subject is an inhibitor of Frizzled receptors.

In one example, said compound or composition that increases the density of peroxisomes in a plurality of cells in the subject is an inhibitor of SFRP1.

In one example, wherein the SFRP1 inhibitor is WAY-316606.

In one example, wherein said compound or composition that increases the density of peroxisomes in a plurality of cells in the subject is an inhibitor of LRP 5/6.

In one example, wherein said compound or composition that increases the density of peroxisomes in a plurality of cells in the subject is a PPAR alpha agonist or a PPAR and gamma agonist.

In one example, wherein said PPAR alpha agonist is Fenofibrate, ciprofibrate, clofibrate, gemfibrozil, bezafibrate, or Elafibranor.

In one example, wherein said PPAR gamma agonist is Rosiglitazone Maleate, Pioglitazone hydrochloride, Lobeglitazone, chiglitazar, KDT-501, Navaglitazar, AVE-0897, ZY-H2, AMG-131, Muraglitazar, Amorfrutins, Formonetin, Bixin, Norbixin, Commipheric acid, Citral, Meranzin, Carnosic acid, Carnosol, Linoleic acid, Saurufuran, Isosilybin A, Gallotannins, or Carvacrol.

In one example, further comprising administering Molnupiravir (MK-4482/EIDD-2801 or Remdesivir to said subject.

In one example, wherein said subject is a human.

In one aspect there is provided a use of a Wnt/β-catenin signaling inhibitor for treating a subject infected with SARS-CoV-2, suspected of being infected with SARS-CoV-2, or at risk of being infected with SARS-CoV-2.

In one aspect there is provided a use of a Wnt/β-catenin signaling inhibitor for in the manufacture of a medicament for treating a subject infected with SARS-CoV-2, suspected of being infected with SARS-CoV-2, or at risk of being infected with SARS-CoV-2.

In one example, wherein said Wnt/β-catenin signaling inhibitor is IWP-O1, IWP-2, IWP-L6, iCRT3, LGK-974, WIK14, Wnt-C59, ICG-001, IWR-1-endo, Silibinin, NCB-0846, KYA1797K, Foxy-5 (Wnt5a mimic peptide), PRI-724, ETC-1922159, PNU-74654, Carnosic acid, Pyrvinium, iCRT-14, Sulindac, SM04755, Famotidine, NSC668036, E7449, Dvl-PDZ Domain Inhibitor II, Olaparib, Niraparib, PJ34 HCl, Capmatinib, Curcumin, or Genistein, triptolide.

In one example, wherein said Wnt/β-catenin signalling inhibitor is Wogonin, Ant1.4Br/Ant1.4Cl, Ipafricept, APCDD1, FzM1, Fz7-21, OTSA101, OTSA101-DTPA-90Y, BNC101, Gigantol, salinomycin, IGFBP-4, DKN-01, Compound 3289-8625, FJ9, NSC668036, peptide Pen-N3, 2X-121, AZ1366, AZ-6102, G007-LK, G244-LM, IWR-1, JW55, JW67, JW74, K-756, MN-64, MSC2504877, NVP-TNKS656, RK-287107, TC-E5001, WIK14, XAV939, TCS 183, 21H7, isoquercitrin, KY1220, MSAB, NRX-252114, BC21, BC2059, CCT031374, CCT036477, CGP049090, CWP232228, ethacrynic acid, FH535, iCRT3, iCRT5, iCRT14, LF3, NLS-StAx-h, PKF115-584, PKF118-310, PKF118-744, PNU-74654, quercetin, ZTM000990, KY-05009, NCB-0846, IQ-1, windorphen, YH249/250, C-82, ICG-001, PRI-724, retinoids, vitamin D3, SAH-BCL9, Adavivint (SM04690, lorecivivint), artesunate, cardamonin, cardionogen, CCT031374, diethyl benzylphosphonate, echinacoside, KY02111, pamidronic acid, or specnuezhenide In one example, further comprising use of Molnupiravir (MK-4482/EIDD-2801 or Remdesivir.

In one example, wherein said subject is a human.

In one aspect there is provided a use of a therapeutically effective amount of a PARP inhibitor for treating a subject infected with SARS-CoV-2, suspected of being infected with SARS-CoV-2, or at risk of being infected with SARS-CoV-2.

In one aspect there is provided a use of a therapeutically effective amount of a PARP inhibitor in the manufacture of a medicament for treating a subject infected with SARS-CoV-2, suspected of being infected with SARS-CoV-2, or at risk of being infected with SARS-CoV-2.

In one example, wherein the PPAR inhibitor is E7449, PJ34 HCl, WIK14, Olaparib and Niraparib are PARP or Tankyrase inhibitors.

In one example, wherein the PARP inhibitor is WIK14, E7449, PJ34 HCl, Olaparib, Talazparib, XAV-939, Veliparib, AZD5305, Fluzoparib, Rucaparib, RBN-2397, PJ34, Pamiparib, G007-LK, JW55, BGP-15, NMS-P118, RBN012759, EB-47 dihydrochloride, AZ6102, RK-287107, GeA-69, MN-64, 5,7,4'-Trimthoxyflavone, Oroxin A, NU0125, BYK204165, K-756, 2-Methylquinazolin-4-ol, AZ-9842, OUL35, Mefuparib hydrochloride, Senaparib, Tankyrase-IN-2, PARP-2-IN-1, BR102375, EB-47, 4'-Methoxychalcone, DR2313, 3-Methoxybenzamide, 5,7-Dihydroxychromone, BRCA1-IN-1, or WD2000-012547.

In one aspect there is provided a use of a compound or a composition that increases the density of peroxisomes in a plurality of cells in a subject, for treating a subject infected with SARS-CoV-2, suspected of being infected with SARS-CoV-2, or at risk of being infected with SARS-CoV-2.

In one aspect there is provided a use of a compound or a composition that increases the density of peroxisomes in a plurality of cells in a subject in the manufacture of a medicament, for treating a subject infected with SARS-CoV-2, suspected of being infected with SARS-CoV-2, or at risk of being infected with SARS-CoV-2.

In one example, wherein said compound or composition that increases the density of peroxisomes in a plurality of cells in the subject is IWP-O1, IWP-2, IWP-L6, iCRT3, LGK-974, WIK14, Wnt-C59, ICG-001, IWR-1-endo, Silibinin, NCB-0846, KYA1797K, Foxy-5 (Wnt5a mimic peptide), PRI-724, ETC-1922159, PNU-74654, Carnosic acid, Pyrvinium, iCRT-14, Sulindac, SM04755, Famotidine, NSC668036, E7449, Dvl-PDZ Domain Inhibitor II, Olaparib, Niraparib, PJ34 HCl, Capmatinib, Curcumin, or Genistein, triptolide.

In one example, wherein said compound or composition that increases the density of peroxisomes in a plurality of cells in the subject is Pyrvinium, KYA1797K, Wnt-C59, ETC-1922159, iCRT-14, SM04755, E7449, IWP-O1, NCB0846, LGK-974, Triptolide or PJ354 HCL.

In one example, wherein said compound or composition that increases the density of peroxisomes in a plurality of cells in the subject is Wogonin, Ant1.4Br/Ant1.4Cl, Ipafricept, APCDD1, FzM1, Fz7-21, OTSA101, OTSA101-

DTPA-90Y, BNC101, Gigantol, salinomycin, IGFBP-4, DKN-01, Compound 3289-8625, FJ9, NSC668036, peptide Pen-N3, 2X-121, AZ1366, AZ-6102, G007-LK, G244-LM, IWR-1, JW55, JW67, JW74, K-756, MN-64, MSC2504877, NVP-TNKS656, RK-287107, TC-E5001, WIKI4, XAV939, TCS 183, 21H7, isoquercitrin, KY1220, MSAB, NRX-252114, BC21, BC2059, CCT031374, CCT036477, CGP049090, CWP232228, ethacrynic acid, FH535, iCRT3, iCRT5, iCRT14, LF3, NLS-StAx-h, PKF115-584, PKF118-310, PKF118-744, PNU-74654, quercetin, ZTM000990, KY-05009, NCB-0846, IQ-1, windorphen, YH249/250, C-82, ICG-001, PRI-724, retinoids, vitamin D3, SAH-BCL9, Adavivint (SM04690, lorecivivint), artesunate, cardamonin, cardionogen, CCT031374, diethyl benzylphosphonate, echinacoside, KY02111, pamidronic acid, or specnuezhenide.

In one example, wherein said compound or composition that increases the density of peroxisomes in a plurality of cells in the subject is an inhibitor of Porcupine.

In one example, wherein the Porcupine inhibitor is CGX1321, GNF-6231, IWP-3, IWP-4, IWP-12, IWP-L6, or RXC004.

In one example, wherein said compound or composition that increases the density of peroxisomes in a plurality of cells in the subject is an inhibitor of β-catenin.

In one example, wherein said compound or composition that increases the density of peroxisomes in a plurality of cells in the subject is an inhibitor of Frizzled receptors.

In one example, wherein said compound or composition that increases the density of peroxisomes in a plurality of cells in the subject is an inhibitor of SFRP1.

In one example, wherein the SFRP1 inhibitor is WAY-316606.

In one example, wherein said compound or composition that increases the density of peroxisomes in a plurality of cells in the subject is an inhibitor of LRP 5/6.

In one example, wherein said compound or composition that increases the density of peroxisomes in a plurality of cells in the subject is a PPAR alpha agonist or a PPAR and gamma agonist.

In one example, wherein said PPAR alpha agonist is Fenofibrate, ciprofibrate, clofibrate, gemfibrozil, bezafibrate, or Elafibranor.

In one example, wherein said PPAR gamma agonist is Rosiglitazone Maleate, Pioglitazone hydrochloride, Lobeglitazone, chiglitazar, KDT-501, Navaglitazar, AVE-0897, ZY-H2, AMG-131, Muraglitazar, Amorfrutins, Formonetin, Bixin, Norbixin, Commipheric acid, Citral, Meranzin, Carnosic acid, Carnosol, Linoleic acid, Saurufuran, Isosilybin A, Gallotannins, or Carvacrol.

In one example, further comprising use of Molnupiravir (MK-4482/EIDD-2801 or Remdesivir.

In one example, wherein said subject is a human.

BRIEF DESCRIPTION OF THE DRAWINGS

Embodiments of the present disclosure will now be described, by way of example only, with reference to the attached Figures.

FIG. 2B. Total RNA extracted from infected cells at 24 hours post infection was subjected to qRT-PCR analysis. The average levels of SARS-CoV-2 viral RNA relative to actin mRNA from 3 independent experiments are shown. Error bars represent standard error of the mean, *p<0.05. FIG. 2C. Cell lysates harvested at 24 hours post-infection were processed for immunoblot analyses with antibodies to SARS-COV2 Spike protein and actin.

FIG. 7A. Relative average viral titers obtained from 3 independent experiments are shown as are the relative cell viabilities of cells treated with Wnt inhibitor for 48 hours in the absence of infection. EC50 and CC50 values were determined and then used to calculate the selectivity indexes (CC50/EC50) for each drug. (FIGS. 7B-7E) Calu3 cells were pre-treated with IWP01, KYA1797K and Pyrvinium at indicated concentrations for 24 hours and then infected with SARS-CoV-2 variants ((FIG. 7B) D614G, (FIG. 7C) UK B.1.1.7, (FIG. 7D) SA B.1.351 and (FIG. 7E) Brazil P.1) using MOI of 0.5. Twenty-four hours later, cell media were subjected to plaque assay. Viral titers from 3 independent experiments were determined and averaged. Error bars represent standard error of the mean, *p<0.05.

DETAILED DESCRIPTION

Figure 1A:
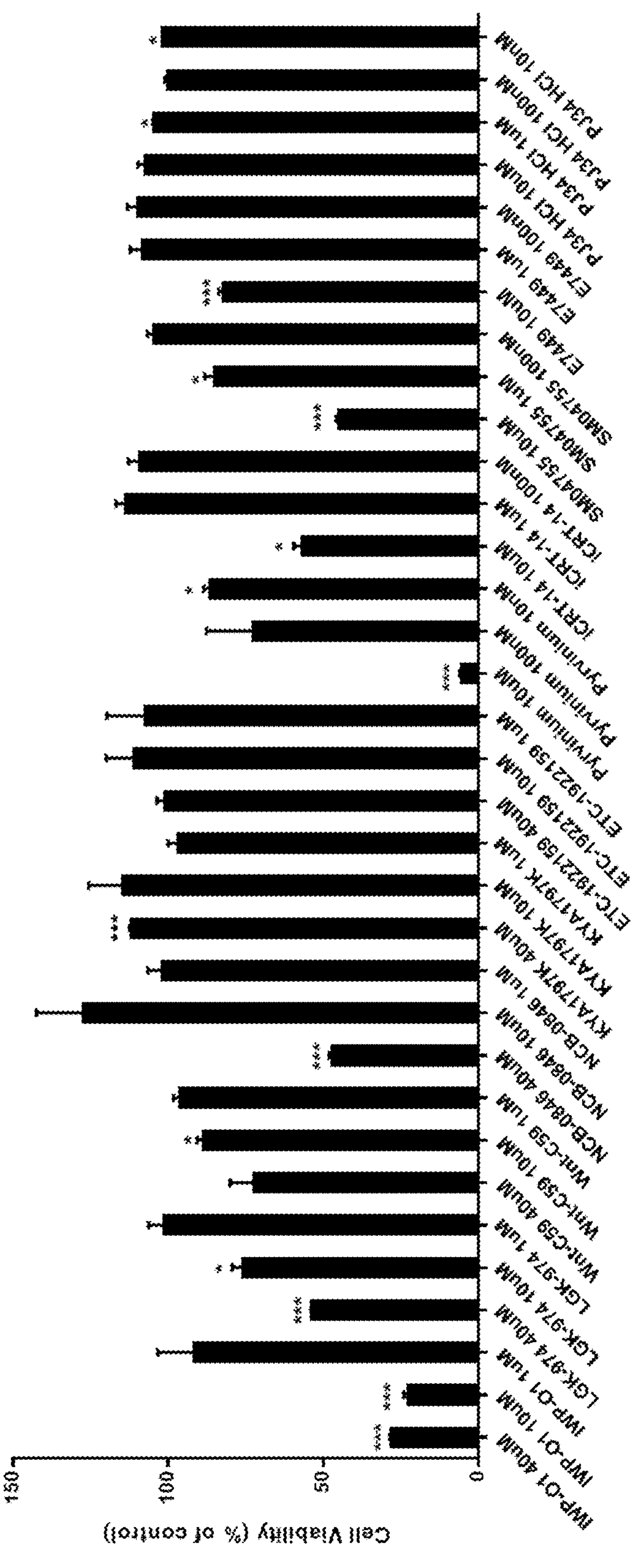
FIGS. 1A-1C. Effect of Wnt/β-catenin inhibitors on cell viability. Calu-3 (FIG. 1A), Normal Human Bronchial Epithelial (NHBE) (FIG. 1B) and A549 (FIG. 1C) cells were treated with the indicated concentrations of Wnt/β-catenin inhibitors or DMSO alone for 72-hours after which the relative cell viabilities were determined using a CELLTITER-GLO® Luminescent Cell Viability Assay kit. The relative average cell viabilities (normalized to DMSO) from 3 independent experiments are shown. Error bars represent standard errors of the means. *, P<0.05; , P<0.01; *, P<0.001 N.S. (not significant)

Generally, the present disclosure provides method of treating infections by SARS-CoV-2, and other pathogenic viruses.

Coronaviruses are a large family of viruses which cause illness in animals and humans. In humans, several coronaviruses are known to cause respiratory infections ranging from the common cold to more severe diseases such as Middle East Respiratory Syndrome (MERS) and Severe Acute Respiratory Syndrome (SARS).

Most recently identified is the 2019 novel coronavirus (SARS-CoV-2 (SCoV2)/COVID-19).

Severe Acute Respiratory Coronavirus 2 (SARS-CoV-2), the causal agent of COVID-19 which was characterized as a pandemic by the World Health Organization (WHO) in March 2020, has triggered an international public health emergency.

The terms "SARS CoV-2", "SCoV2", and "COVID-19", may be used interchangeably.

The WHO reports that as of Jul. 23 2021, there have been 192,284,207 confirmed cases of COVID-19, including 4,136,518 deaths, A number of variants of SARS-CoV-2 have been identified. Variants are viruses that have changed or mutated. Variants are common with coronaviruses. A variant form may confer an evolutionary advantage or disadvantage relative to a progenitor form or may be neutral.

In some examples, a SARS-CoV-2 isolate is a Variant of Interest (VOI) if, compared to a reference isolate, its genome has mutations with established or suspected phenotypic implications, and either: has been identified to cause community transmission/multiple COVID-19 cases/clusters, or has been detected in multiple countries; or is otherwise assessed to be a VOI by (for example) WHO in consultation with the WHO SARS-CoV-2 Virus Evolution Working Group.

Currently designated Variants of Concern (VOC) by the WHO

| WHO label | Pango lineages | GISAID clade | Nextstrain clade | Additional amino acid changes monitored* | Earliest documented samples | Date of designation |
|---|---|---|---|---|---|---|
| Alpha | B.1.1.7 | GRY | 20I (V1) | +S: 484K +S: 452R | United Kingdom, September 2020 | 18 Dec. 2020 |
| Beta | B.1.351 B.1.351.2 B.1.351.3 | GH/501Y.V2 | 20H (V2) | +S: L18F | South Africa, May 2020 | 18 Dec. 2020 |
| Gamma | P.1 P.1.1 P.1.2 | GR/501Y.V3 | 20J (V3) | +S: 681H | Brazil, November 2020 | 11 Jan. 2021 |
| Delta | B.1.617.2 AY.1 AY.2 AY.3 | G/478K.V1 | 21A | +S: 417N | India, October 2020 | VOI: 4 Apr. 2021 VOC: 11 May 2021 |

In some examples, a SARS-CoV-2 variant of concern (VOC) is a variant that meets the definition of a VOI and, through a comparative assessment, has been demonstrated to be associated with one or more of the following changes at a degree of global public health significance: Increase in transmissibility or detrimental change in COVID-19 epidemiology; or Increase in virulence or change in clinical disease presentation; or Decrease in effectiveness of public health and social measures or available diagnostics, vaccines, therapeutics.

Currently designated Variants of Interest (VOI)

| WHO label | Pango lineages | GISAID clade | Nextstrain clade | Earliest documented samples | Date of designation |
|---|---|---|---|---|---|
| Eta | B.1.525 | G/484K.V3 | 21D | Multiple countries, December 2020 | 17 Mar. 2021 |
| Iota | B.1.526 | GH/253G.V1 | 21F | United States of America, November 2020 | 24 Mar. 2021 |
| Kappa | B.1.617.1 | G/452R.V3 | 21B | India, October 2020 | 4 Apr. 2021 |
| Lambda | C.37 | GR/452Q.V1 | 21G | Peru, December 2020 | 14 Jun. 2021 |

Other naming systems are being developed for variants of SARS-CoV-2.

In some examples, there is provided a method of treating a subject infected with SARS-CoV-2, suspected of being infected with SARS-CoV-2, or at risk of being infected with SARS-CoV-2, comprising or consisting of, administering a therapeutically effective amount of a Wnt/β-catenin signaling inhibitor.

In some examples, there is provided a method of treating a subject infected with SARS-CoV-2, suspected of being infected with SARS-CoV-2, or at risk of being infected with SARS-CoV-2, comprising or consisting of, administering a therapeutically effective amount of a compound or composition that increases the density of peroxisomes in a plurality of cells in the subject.

In some examples, there is provided a method of treating a subject infected with SARS-CoV-2, suspected of being infected with SARS-CoV-2, or at risk of being infected with SARS-CoV-2, comprising or consisting of, administering a therapeutically effective amount of a PARP inhibitor.

In some examples, a compound or composition that inhibits the following targets in the Wnt pathway may increase the density of peroxisomes in a cell in a subject, including, but not limited to Porcupine, β-catenin, TCF/LEF, Frizzled receptors, SFRP1 or LRP 5/6. In some examples Pyrvinium, KYA1797K, Wnt-C59, ETC-1922159, iCRT-14, SM04755, E7449, IWP-O1, NCB0846, LGK-974, Triptolide or PJ354 HCL, may be used.

In some examples, Porcupine inhibitors include but are not limited to CGX1321, GNF-6231, IWP-3, IWP-4, IWP-12, IWP-L6, or RXC004.

In some examples, SFRP1 inhibitors include but are not limited to WAY-316606.

In some examples, the Wnt/β-catenin signaling inhibitor is IWP-O1, IWP-2, IWP-L6, iCRT3, LGK-974, WIK14, Wnt-C59, ICG-001, IWR-1-endo, Silibinin, NCB-0846, KYA1797K, Foxy-5 (Wnt5a mimic peptide), PRI-724, ETC-1922159, PNU-74654, Carnosic acid, Pyrvinium, iCRT-14, Sulindac, SM04755, Famotidine, NSC668036, E7449, Dvl-PDZ Domain Inhibitor II, Olaparib, Niraparib, PJ34 HCl, Capmatinib, Curcumin, or Genistein, triptolide.

In some examples, the Wnt/β-catenin signaling inhibitor includes but is not limited to Wogonin, Ant1.4Br/Ant1.4Cl, Ipafricept, APCDD1, FzM1, Fz7-21, OTSA101, OTSA101-DTPA-90Y, BNC101, Gigantol, salinomycin, IGFBP-4, DKN-01, Compound 3289-8625, FJ9, NSC668036, peptide Pen-N3, 2X-121, AZ1366, AZ-6102, G007-LK, G244-LM, IWR-1, JW55, JW67, JW74, K-756, MN-64, MSC2504877, NVP-TNKS656, RK-287107, TC-E5001, WIKI4, XAV939, TCS 183, 21H7, isoquercitrin, KY1220, MSAB, NRX-252114, BC21, BC2059, CCT031374, CCT036477, CGP049090, CWP232228, ethacrynic acid, FH535, iCRT3, iCRT5, iCRT14, LF3, NLS-StAx-h, PKF115-584, PKF118-310, PKF118-744, PNU-74654, quercetin, ZTM000990, KY-05009, NCB-0846, IQ-1, windorphen, YH249/250, C-82, ICG-001, PRI-724, retinoids, vitamin D3, SAH-BCL9, Adavivint (SM04690, lorecivivint), artesunate, cardamonin, cardionogen, CCT031374, diethyl benzylphosphonate, echinacoside, KY02111, pamidronic acid, or specnuezhenide.

In some examples, there is provided a method of treating a subject infected with SARS-CoV-2, suspected of being infected with SARS-CoV-2, or at risk of being infected with SARS-CoV-2, comprising or consisting of, administering a therapeutically effective amount of a PARP inhibitor.

In some examples, the PPAR inhibitor includes but is not limited to E7449, PJ34 HCl, WIK14, Olaparib and Niraparib are PARP and/or Tankyrase inhibitors.

In some example, the PARP inhibitor includes, but is not limited to WIK14, E7449, PJ34 HCl, Olaparib, Talazparib, XAV-939, Veliparib, AZD5305, Fluzoparib, Rucaparib, RBN-2397, PJ34, Pamiparib, G007-LK, JW55, BGP-15, NMS-P118, RBN012759, EB-47 dihydrochloride, AZ6102, RK-287107, GeA-69, MN-64, 5,7,4'-Trimthoxyflavone, Oroxin A, NU0125, BYK204165, K-756, 2-Methylquinazolin-4-ol, AZ-9842, OUL35, Mefuparib hydrochloride, Senaparib, Tankyrase-IN-2, PARP-2-IN-1, BR102375, EB-47, 4'-Methoxychalcone, DR2313, 3-Methoxybenzamide, 5,7-Dihydroxychromone, BRCA1-IN-1, or WD2000-012547.

In some examples, the compound/composition that increase peroxisome density include IWP-O1, IWP-2, IWP-L6, iCRT3, LGK-974, WIK14, Wnt-C59, ICG-001, IWR-1-endo, Silibinin, NCB-0846, KYA1797K, Foxy-5 (Wnt5a mimic peptide), PRI-724, ETC-1922159, PNU-74654, Carnosic acid, Pyrvinium, iCRT-14, Sulindac, SM04755, Famotidine, NSC668036, E7449, Dvl-PDZ Domain Inhibitor II, Olaparib, Niraparib, PJ34 HCl, Capmatinib, Curcumin, or Genistein, triptolide.

In other examples, the compound/composition that increases peroxisome density includes but is not limited to, Pyrvinium, KYA1797K, Wnt-C59, ETC-1922159, iCRT-14, SM04755, E7449, IWP-O1, NCB0846, LGK-974, Triptolide or PJ354 HCL.

In some examples, other compound/composition that may increase peroxisome density include but are not limited to Wogonin, Ant1.4Br/Ant1.4Cl, Ipafricept, APCDD1, FzM1, Fz7-21, OTSA101, OTSA101-DTPA-90Y, BNC101, Gigantol, salinomycin, IGFBP-4, DKN-01, Compound 3289-8625, FJ9, NSC668036, peptide Pen-N3, 2X-121, AZ1366, AZ-6102, G007-LK, G244-LM, IWR-1, JW55, JW67, JW74, K-756, MN-64, MSC2504877, NVP-TNKS656, RK-287107, TC-E5001, WIKI4, XAV939, TCS 183, 21H7, isoquercitrin, KY1220, MSAB, NRX-252114, BC21, BC2059, CCT031374, CCT036477, CGP049090, CWP232228, ethacrynic acid, FH535, iCRT3, iCRT5, iCRT14, LF3, NLS-StAx-h, PKF115-584, PKF118-310, PKF118-744, PNU-74654, quercetin, ZTM000990, KY-05009, NCB-0846, IQ-1, windorphen, YH249/250, C-82, ICG-001, PRI-724, retinoids, vitamin D3, SAH-BCL9, Adavivint (SM04690, lorecivivint), artesunate, cardamonin, cardionogen, CCT031374, diethyl benzylphosphonate, echinacoside, KY02111, pamidronic acid, or specnuezhenide In some examples, PPAR alpha and gamma agonists may be used to increase peroxisome density in a cell.

In some examples, the PPAR gamma agonists (Rosiglitazone Maleate and Pioglitazone hydrochloride) inhibit SARS-CoV-2 replication In some examples, other PPAR gamma agonists include but are not limited to Lobeglitazone, chiglitazar, KDT-501, Navaglitazar, AVE-0897, ZY-H2, AMG-131, Muraglitazar, Amorfrutins, Formonetin, Bixin, Norbixin, Commipheric acid, Citral, Meranzin, Carnosic acid, Carnosol, Linoleic acid, Saurufuran, Isosilybin A, Gallotannins, or Carvacrol, As show herein, Pioglitazone hydrochloride and chiglitazar upregulate type I interferon.

In some examples, PPAR alpha agonists include but are not limited to Fenofibrate, ciprofibrate, clofibrate, gemfibrozil, bezafibrate, or Elafibranor.

In some examples, the compounds are a tautomer, or a pharmaceutically acceptable salt, or a solvate, or a functional derivative thereof.

The term "functional derivative" as used herein refers to a molecule that retains a biological activity (either function or structural) that is substantially similar to that of the original compound. A functional derivative or equivalent may be a natural derivative or is prepared synthetically.

Also encompassed as prodrugs or "physiologically functional derivative".

The term "physiologically functional derivative" as used herein refers to compounds which are not pharmaceutically active themselves but which are transformed into their pharmaceutically active form in vivo, i.e. in the subject to which the compound is administered.

The term "prodrug" as used herein, refers to a derivative of a substance that, following administration, is metabolized in vivo, e.g. by hydrolysis or by processing through an enzyme, into an active metabolite.

The term "subject", as used herein, refers is to an individual. Non-limiting examples of a subject may include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject may be a mammal such as a primate or a human.

In a specific example, the subject is a human.

The term "infection" "or infected" as used herein, refers to a disease or condition attributable to the presence in a host of a foreign organism or agent that reproduces within the host. Infections typically involve breach of a normal mucosal or other tissue barrier by an infectious organism or agent. In some examples, the infection is infection with SARS CoV-2.

A subject that has an infection is a subject having objectively measurable infectious organisms or agents present in the subject's body.

A subject at risk of having an infection is a subject that is predisposed to develop an infection. Such a subject can include, for example, a subject with a known or suspected exposure to an infectious organism or agent. A subject at risk of having an infection also can include a subject with a condition associated with impaired ability to mount an immune response to an infectious organism or agent.

In some examples, a subject identified as having SARS CoV-2 may be treated.

The term "treatment", "treat", or "treating" as used herein, refers to obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment.

The term "amelioration" or "ameliorates" as used herein refers to a decrease, reduction or elimination of a condition, disease, disorder, or phenotype, including an abnormality or symptom.

The term "symptom" of a disease or disorder is any morbid phenomenon or departure from the normal in structure, function, or sensation, experienced by a subject and indicative of disease.

A "treatment regimen" as used herein refers to a combination of dosage, frequency of administration, or duration of treatment, with or without addition of a second medication.

For example, a subject infected with SARS-CoV-2 can be treated to prevent progression or alternatively a subject in remission can be treated with a compound or composition described herein to prevent recurrence.

In some examples, there is described a composition comprising a compound as described herein, and a pharmaceutically acceptable carrier, diluent, or vehicle.

A compound or composition may be administered alone or in combination with other treatments, either simultaneously or sequentially, dependent upon the condition to be treated.

In treating a subject, a therapeutically effective amount may be administered to the subject.

As used herein, the term "therapeutically effective amount" refers to an amount that is effective for preventing, ameliorating, or treating a disease or disorder.

The formulations may conveniently be presented in unit dosage form and may be prepared by any methods well known in the art of pharmacy. Such methods include the step of bringing the active compound into association with a carrier, which may constitute one or more accessory ingredients. In general, the formulations are prepared by uniformly and intimately bringing into association the active compound with liquid carriers or finely divided solid carriers or both, and then if necessary shaping the product.

The compounds and compositions may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot/for example, subcutaneously or intramuscularly.

Compounds and/or compositions comprising compounds disclosed herein may be used in the methods described herein in combination with standard treatment regimes, as would be known to the skilled worker.

In some examples, a subject may also be treated with nucleoside analogs Molnupiravir (MK-4482/EIDD-2801 or Remdesivir or together with therapeutic monoclonal antibodies.

In some examples, therapeutic formulations comprising the compounds or compositions as described herein may be prepared for by mixing compounds or compositions having the desired degree of purity with optional physiologically acceptable carriers, excipients or stabilizers, in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The therapeutic formulation may also contain more than one active compound as necessary for the particular indication being treated, typically those with complementary activities that do not adversely affect each other. Such molecules are suitably present in combination in amounts that are effective for the purpose intended.

Method of the invention are conveniently practiced by providing the compounds and/or compositions used in such method in the form of a kit. Such kit preferably contains the composition. Such a kit preferably contains instructions for the use thereof.

To gain a better understanding of the invention described herein, the following examples are set forth. It should be understood that these examples are for illustrative purposes only. Therefore, they should not limit the scope of this invention in anyway.

EXAMPLES

Example 1

Abstract

Severe Acute Respiratory Syndrome Coronavirus 2 (SARS-CoV-2) is responsible for the most devastating global pandemic over the last 100 years. While newly approved vaccines have proven highly effective in curbing serious illness and viral spread, there remains a need for antiviral drugs against SARS-CoV-2. Understanding how SARS-CoV-2 affects cellular pathways during infection may facility development of host cell-targeted therapeutics with broad-spectrum antiviral activity. The interferon system is critical for reducing replication and pathogenesis of many viruses including SARS-CoV-2. While mitochondria have long been known to function in the induction phase of the interferon response, more recently it has become clear that peroxisomes perform similar roles in antiviral defense. The importance of peroxisomes in controlling viral replication is supported by the fact that a growing number of viruses are known to downregulate peroxisome formation and that genetically inducing peroxisome biogenesis inhibits virus replication. Here, we show that multiple drugs that block Wnt/β-catenin signaling have potent antiviral activity against SARS-CoV-2. Together, our data suggest that this class of drugs have prophylactic and/or therapeutic value for treatment of SARS-CoV-2 and potentially other emerging viral pathogens.

Results

Wnt/β-Catenin Signaling Inhibitors Reduce SARS-CoV-2 Titre and Replication

Figure 1B:
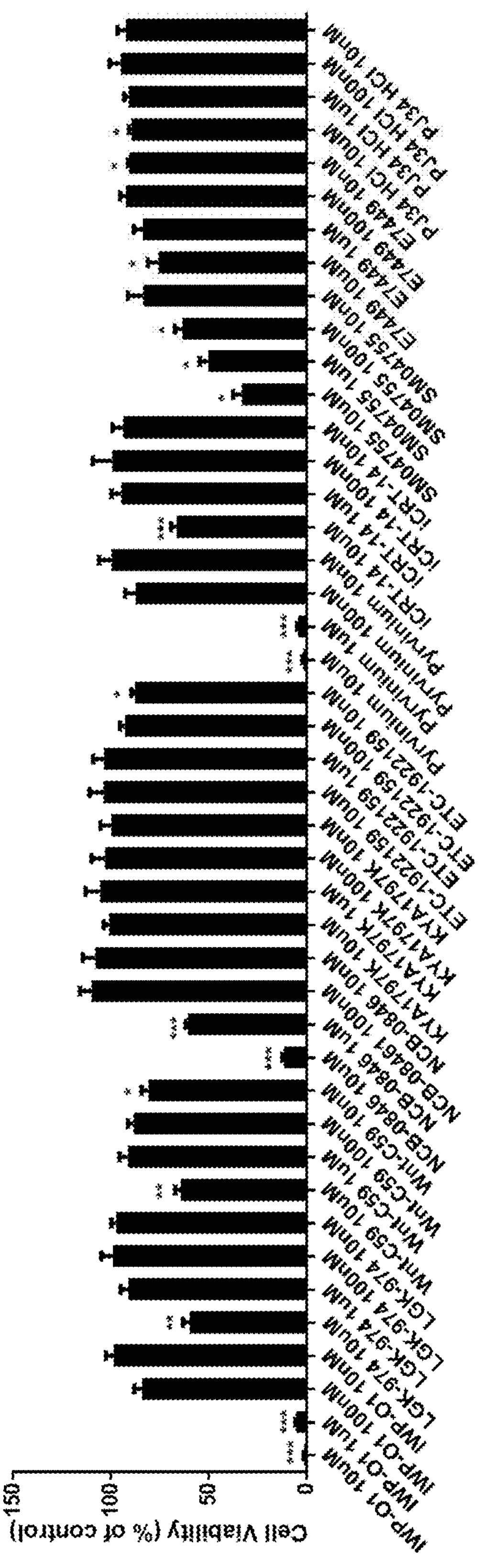
Figure 1C:
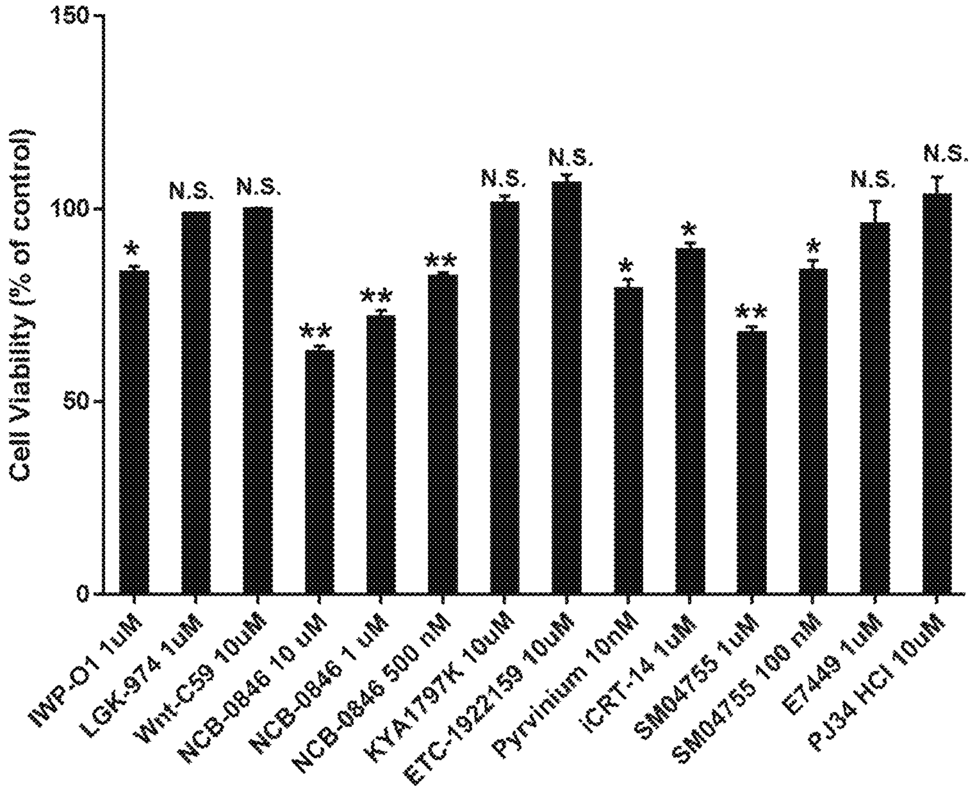

Peroxisomes are metabolic organelles that also have important roles in antiviral signaling 1-3. We hypothesized that drugs that block the Wnt/β-catenin pathway would induce peroxisome proliferation and potentiate the cellular antiviral response. To address this hypothesis, Calu-3 cells were treated with a battery of commercially available Wnt/β-catenin signaling inhibitors (0.1 to 1 μM) or DMSO alone and then infected with SARS-CoV-2 (CANADA/ON- VIDO-01/2020 isolate). None of the drugs showed any significant cytotoxicity at these concentrations (FIG. 1). Culture media as well as RNA and proteins extracted from cells were collected 24- and 48-hours post-infection. Viral titers were determined by plaque assay and viral genomic RNA and viral spike protein levels were assessed by qRT-PCR and immunoblotting respectively.

Figure 2A:
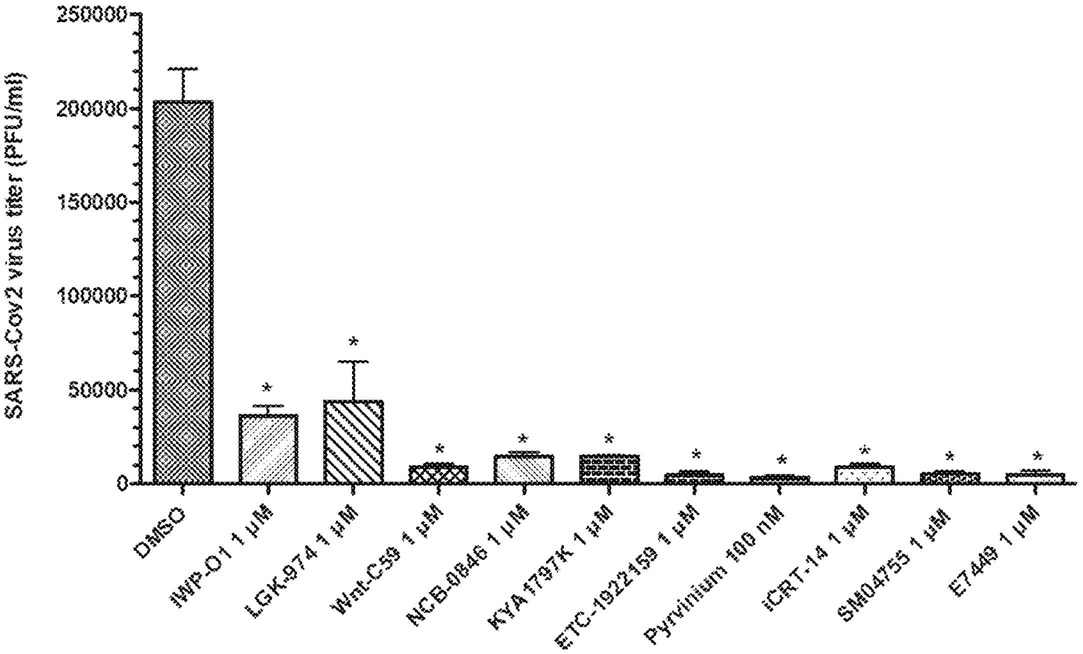
FIGS. 2A-2C. Wnt inhibitors significantly reduce SARS-COV2 virus titer and replication in Calu3 cells. Calu3 cells were pre-treated with the indicated Wnt inhibitors (1 μM) or Pyrvinium (100 nM) for 24 hours and then infected with SARS-CoV-2 (CANADA/VIDO01/2020 strain) using MOI of 0.5. Twenty-four hours later, media were collected and subjected to plaque assay to determine viral titers (FIG. 2A). Data shown are averaged from 3 independent experiments. Error bars represent standard error of the mean, *p<0.05.
Figure 2B:
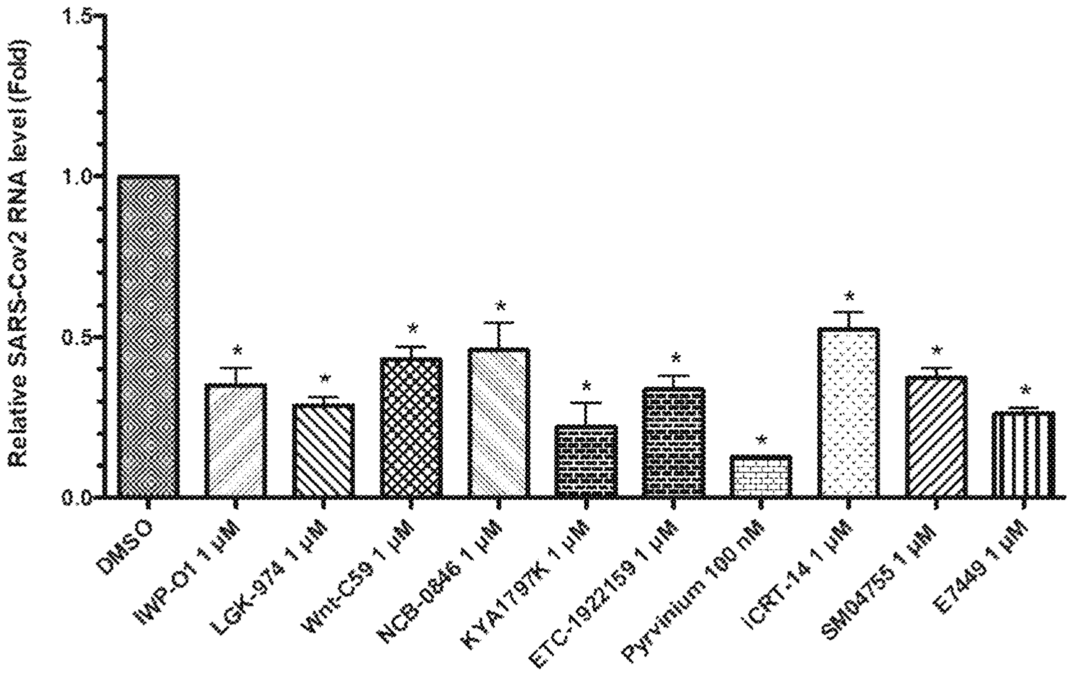
Figure 2C:
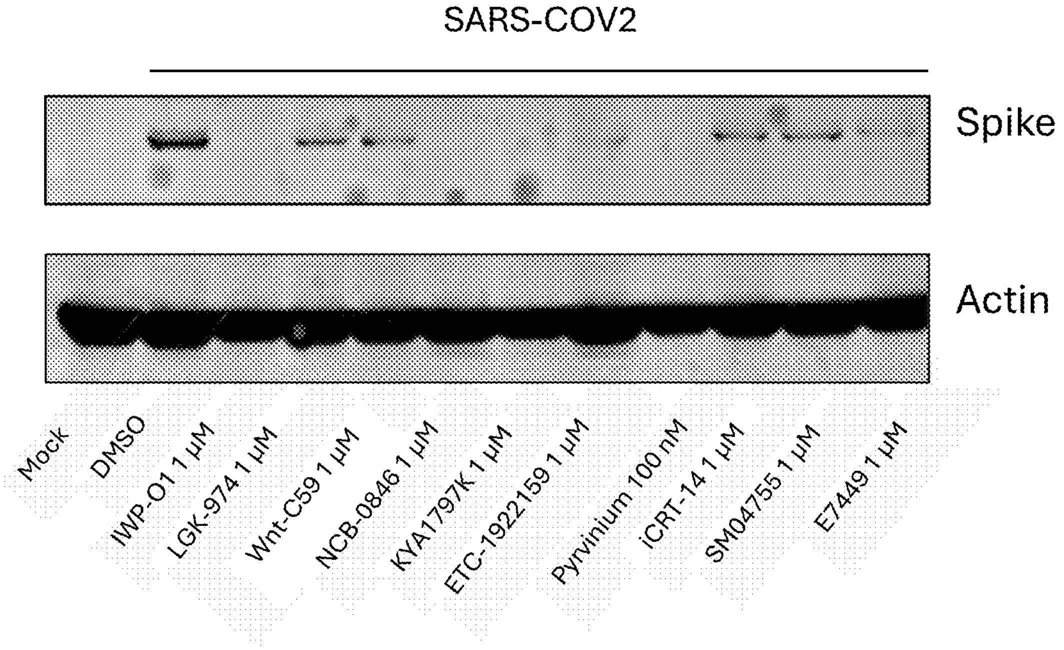
Figure 3:
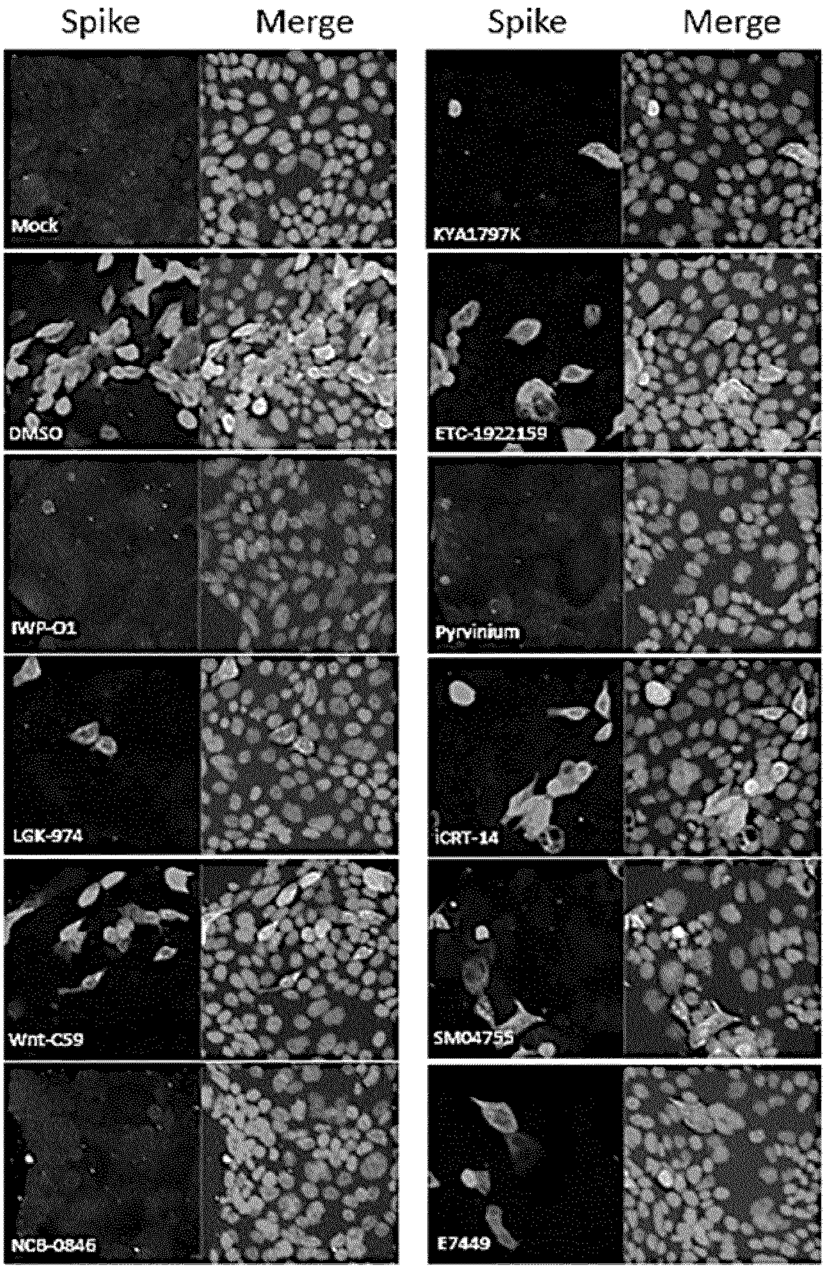
FIG. 3. Wnt/b-catenin inhibitors reduce SARS-CoV-2 infection. Calu3 cells grown on coverslips were pre-treated with Wnt inhibitors at 1 μM concentration except for Pyrvinium which was used at 100 nM for 24-hours and then infected with SARS-CoV-2 (CANADA/VIDO01/2020 strain) using MOI of 0.5. Twenty-four hours, cells were processed for indirect immunofluorescence and confocal microscopy using a mouse monoclonal antibody to Spike protein and donkey anti-mouse IgG conjugated to Alexa Fluor 488. Nuclei were stained using DAPI.
Figure 4A:
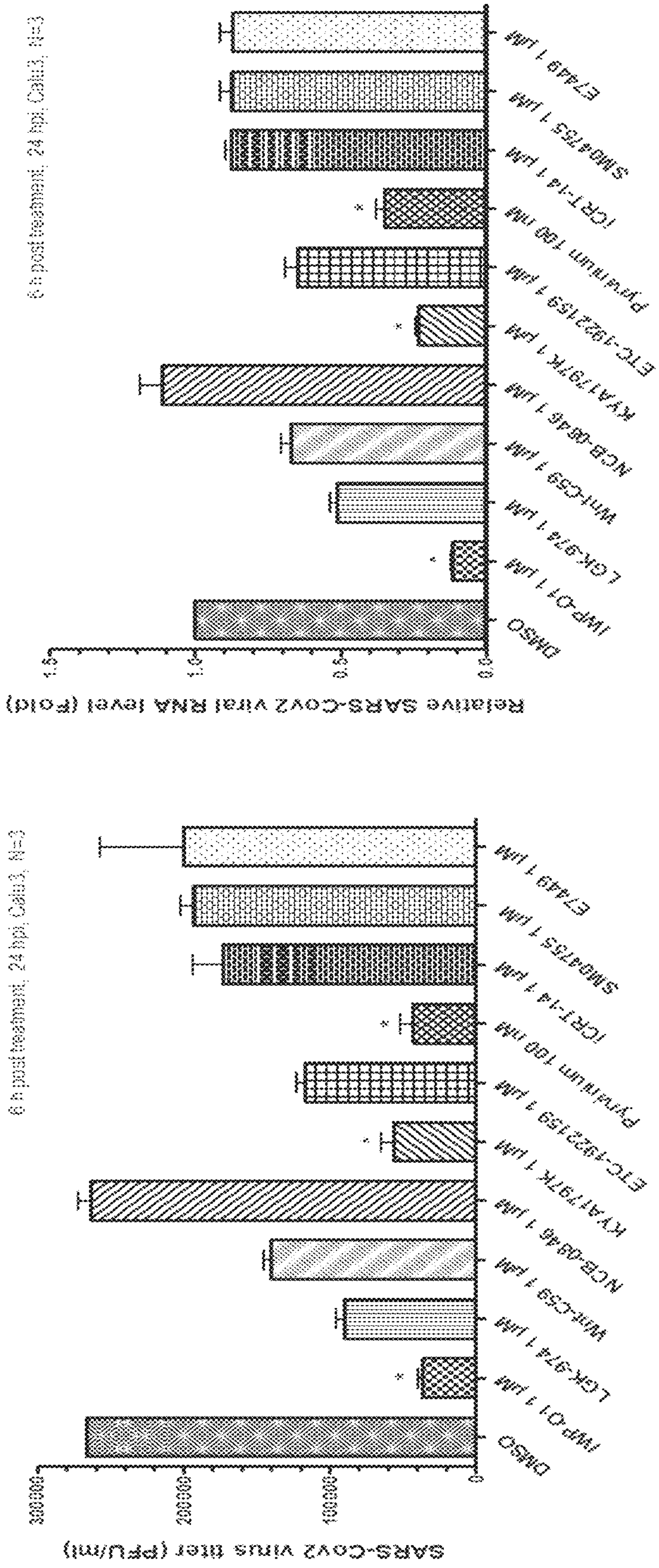
FIGS. 4A-4B. The Wnt/b-catenin inhibitors IWP01, KYA1797K and Pyrvinium reduce SARS-CoV-2 replication when added 6-hours post-infection. Calu3 cells were infected with SARS-CoV-2 (CANADA/VIDO01/2020 strain, MOI of 0.5) for 6-hours after which IWP01 (1 μM), KYA1797K (1 μM) or Pyrvinium (100 nM) were added. Twenty-four (FIG. 4A) and forty-eight (FIG. 4B) hours later, virus-containing media were subjected to plaque assays (left panels) and total RNA extracted from cells was subjected to qRT-PCR to determine relative levels of viral RNA (right panels). Average viral titers and genomic RNA levels from drug-treated cells from 3 independent experiments are shown (FIG. 4A and FIG. 4B, left panels). Error bars represent standard error of the mean, *p<0.05.
Figure 4B:
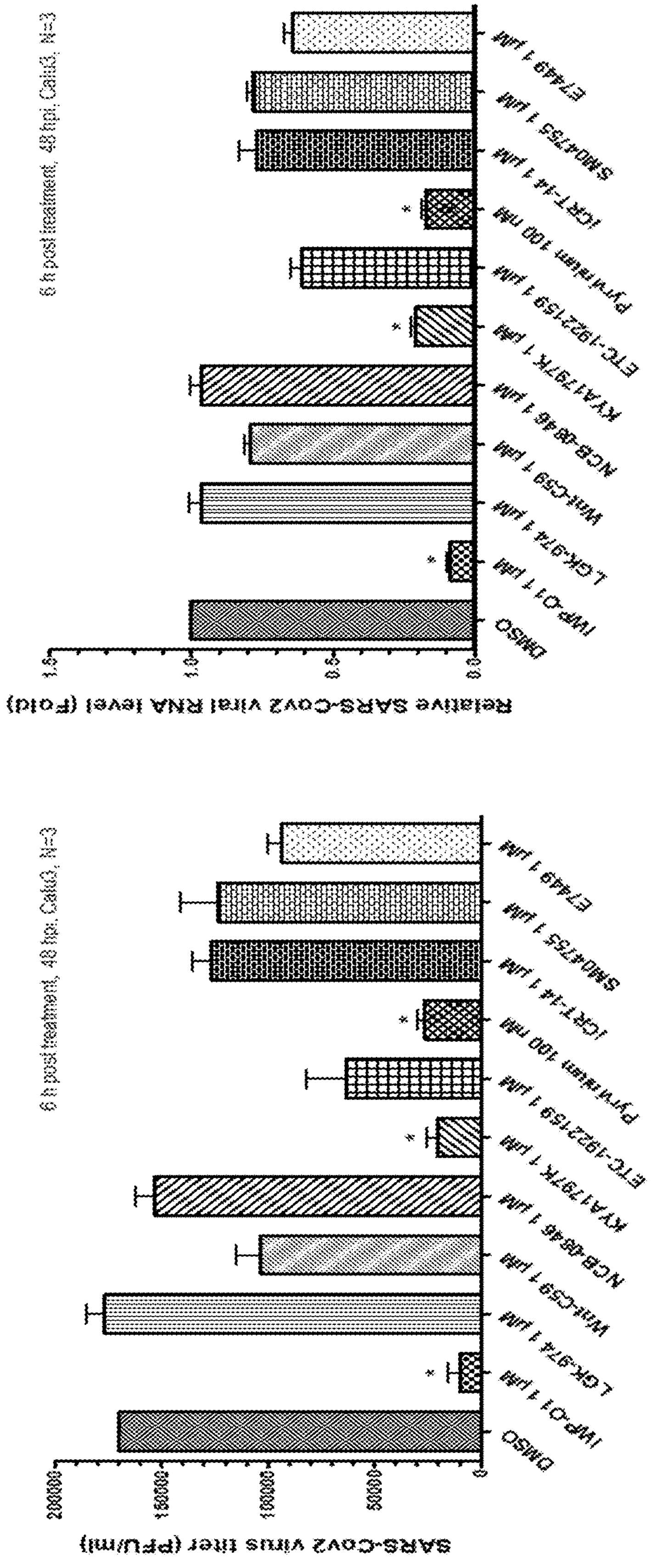
Figure 5A:
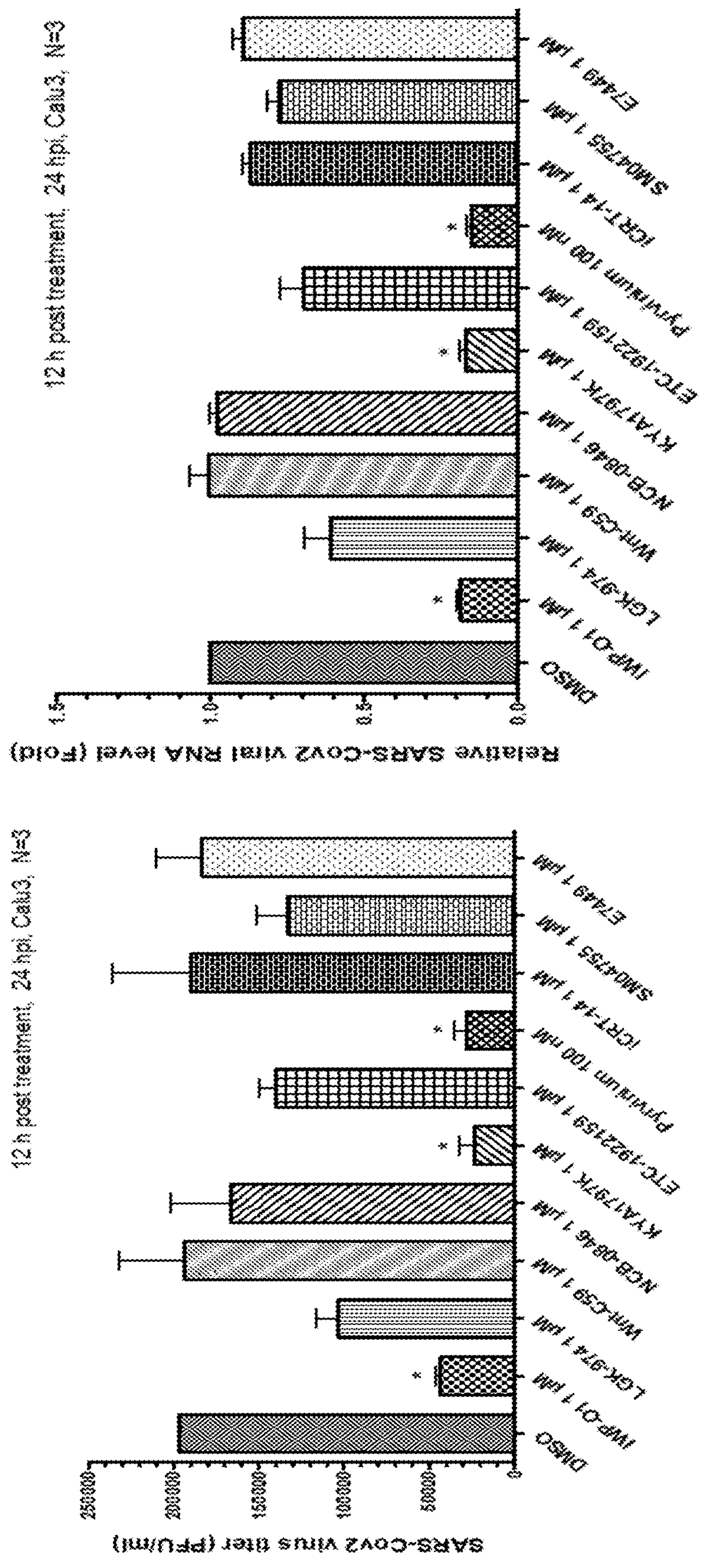
FIGS. 5A and 5B. The Wnt/b-catenin inhibitors IWP01, KYA1797K and Pyrvinium reduce SARS-CoV-2 replication when added 12-hours post-infection. Calu3 cells were infected with SARS-CoV-2 (CANADA/VIDO01/2020 strain, MOI of 0.5) for 12-hours after which IWP01 (1 μM), KYA1797K (1 μM) or Pyrvinium (100 nM) were added. Twenty-four (FIG. 5A) and forty-eight (FIG. 5B) hours later, virus-containing media were subjected to plaque assays (left panels) and total RNA extracted from cells was subjected to qRT-PCR to determine relative levels of viral RNA (right panels). Average viral titers and genomic RNA levels from drug-treated cells from 3 independent experiments are shown (FIG. 5A and FIG. 5B, left panels). Error bars represent standard error of the mean, *p<0.05.
Figure 5B:
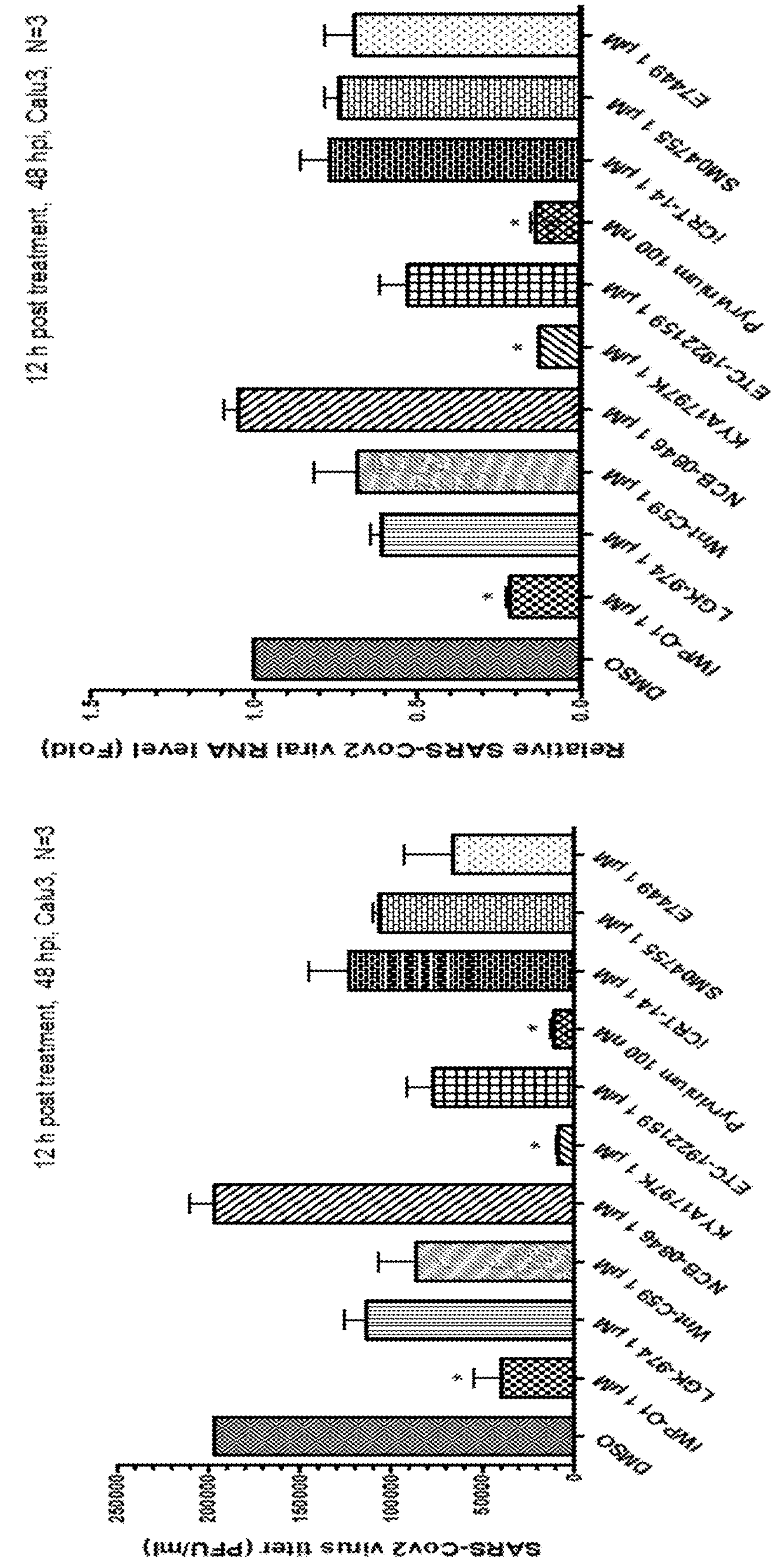

Results from the 10 Wnt/β-catenin inhibitors with the most potent antiviral activities are shown in FIG. 2. All of the inhibitors reduced viral titers by at least 80% and as much as 98% under the conditions employed (FIG. 2A). Similarly, all of these drugs reduced levels of viral genomic RNA levels (48-87%) suggesting that virus replication was impaired (FIG. 2B) by drug treatment. Viral spike protein was reduced or undetectable in drug-treated samples (FIG. 2C). Indirect immunofluorescence analyses revealed that Wnt/β-catenin inhibitors dramatically reduced the proportion of Calu-3 cells that became infected with SARS-CoV-2 (FIG. 3). Some Wnt/β-catenin inhibitors were also effective in reducing SARS-CoV-2 replication when added to Calu-3 cells 6 and 12-hours after infection (FIGS. 4 and 5). Specifically, viral titers and genomic RNA levels were decreased by 77-94% and 65-91% respectively in IWP-O1-, KYA1797K- and Pyrvinium-treated samples.

Figure 6:
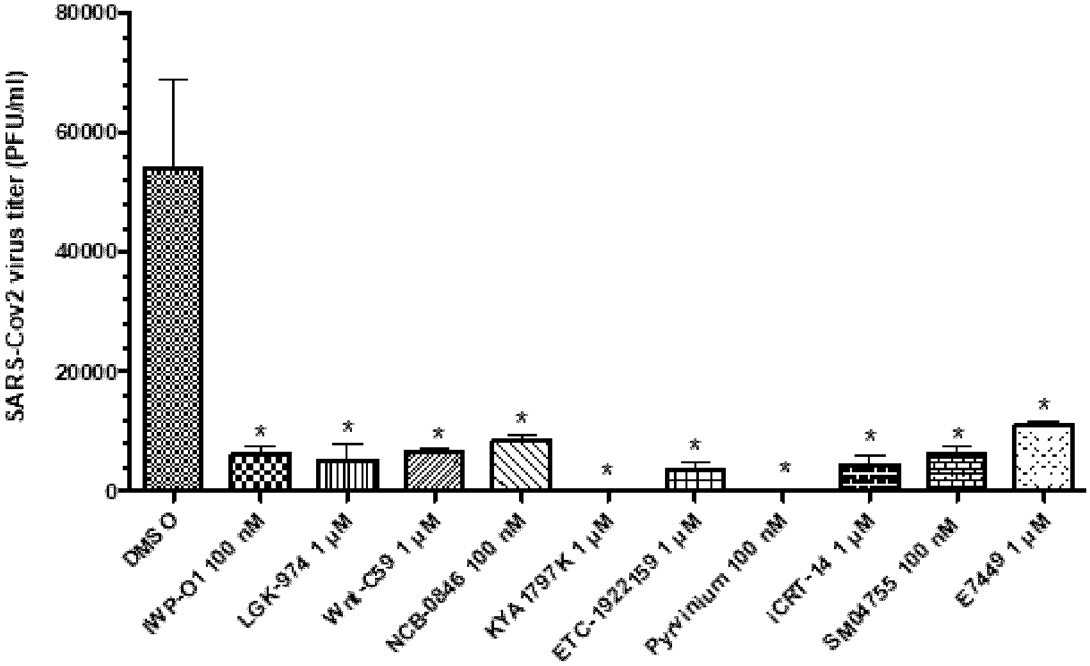
FIG. 6. Wnt inhibitors significantly reduce SARS-COV2 virus titer in normal bronchial epithelial (NHBE) lung cells. Primary human NHBE cells were pre-treated with Wnt inhibitors at indicated concentrations for 24 hours and then infected with SARS-CoV-2 (CANADA/VIDO01/2020 strain) using MOI of 0.5 for 24 hours. Virus-containing media were then subjected to plaque assay to determine viral titers. The average titers from 3 independent experiments are shown. Error bars represent standard error of the mean, *p<0.05.

To determine if the Wnt/β-catenin inhibitors were also effective in blocking replication of SARS-CoV-2 in primary cells, normal human bronchial epithelial (NHBE) lung cells obtained from bronchoscopy patients, were infected in the presence of absence of drugs or DMSO alone. Plaque assay data in FIG. 6 show that Wnt/β-catenin inhibitors were even more potent in reducing replication of SARS-CoV-2 in NHBE cells. Specifically, no infectious virus was detected in the media of infected cells pre-treated with KYA1797K or Pyrvinium.

Figure 7A:
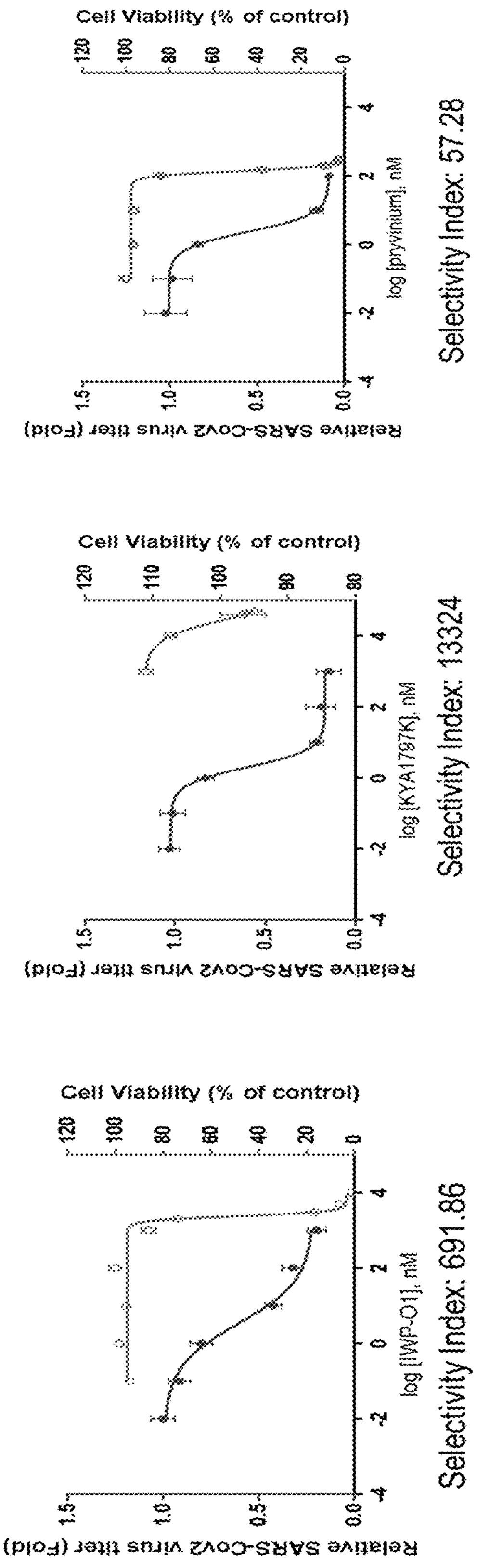
FIGS. 7A-7E. Wnt inhibitors inhibit replication of SARS-CoV-2 variants of concern. Calu3 cells were pre-treated with the indicated concentrations of Wnt inhibitors IWP01, KYA1797K and Pyrvinium (0.01 nM to 1 mM) for 24 hours and then infected with SARS-CoV-2 (CANADA/VIDO01/2020 strain) using MOI of 0.5. Twenty-four hours later, cell media and lysates were collected and subjected to plaque and cytotoxicity assays to determine viral titers and cell viability respectively.
Figure 7B:
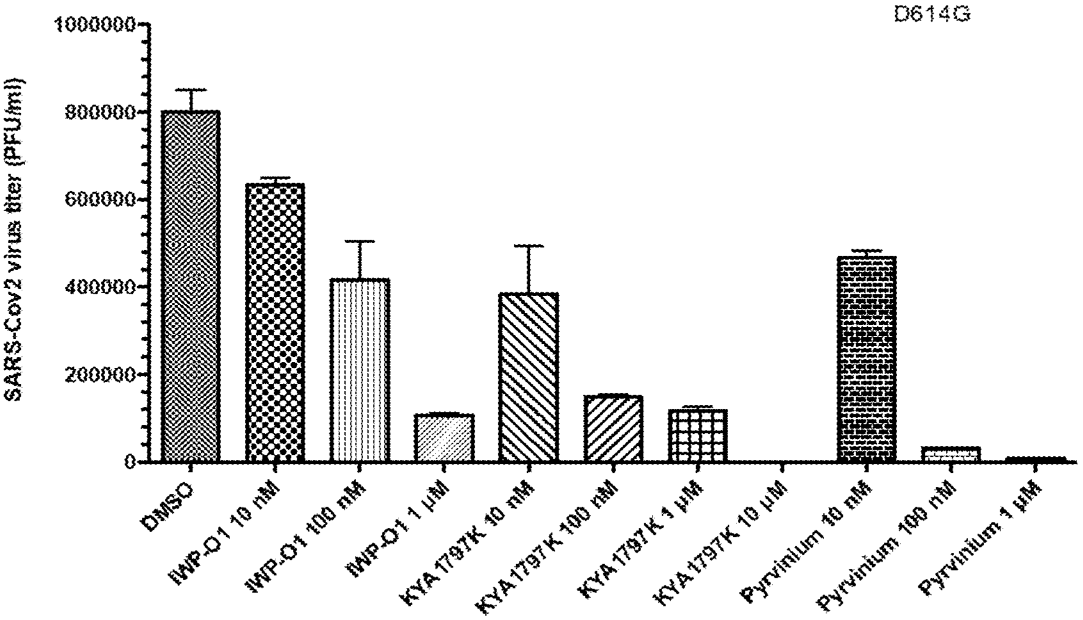
Figure 7C:
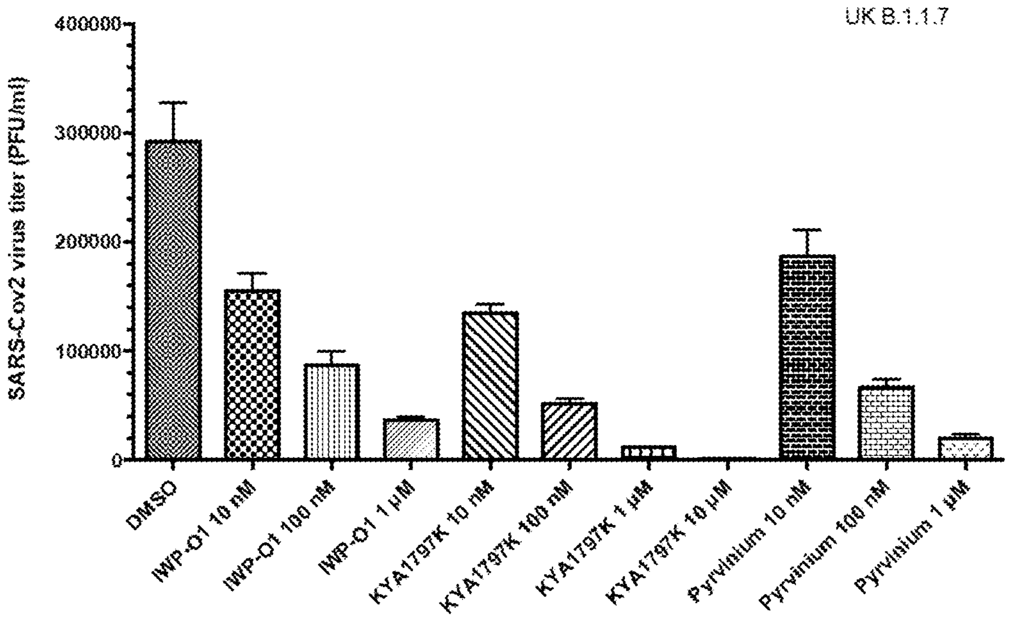
Figure 7D:
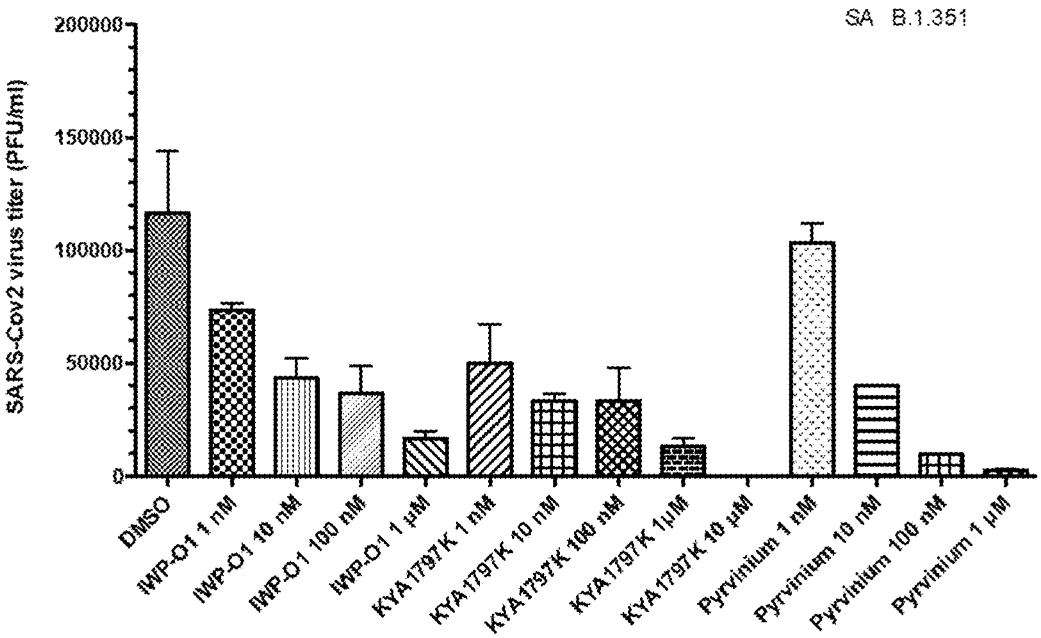

The experiments described above were performed with an early isolate of SARS-CoV-2 (CANADA/ON-VIDO-01/2020) that preceded the emergence of D614G strains and variants of concern. To determine whether Wnt/β-catenin inhibitors were effective against newer variants, tested the antiviral activities of IWP-O1, KYA1797K and Pyrvinium against Calu-3 cells infected with D614G, alpha, beta and gamma variants of SARS-CoV-2. Among the 10 Wnt/β-catenin inhibitors tested above, IWP-O1, KYA1797K and Pyrvinium were chosen because they have low EC50 values (<5 nM) and high selectivity indexes ranging from 57 to 13,324 (FIG. 7A). In addition, as indicated above, all three drugs inhibit virus replication when added pre- or post-infection. Calu-3 cells were pre-treated with IWP01, KYA1797K and Pyrvinium at indicated concentrations for 24 hours and then infected with D614G, alpha, beta and gamma variants of SARS-CoV-2 (MOI of 0.5) for 24-hours after which media were collected for plaque assays. Results in FIG. 3 B-E show that IWP01 (1 μM), KYA1797K (1 μM) and Pyrvinium (100 nM) reduce SARS-CoV-2 variant titers by 84-87%, 85-96% and 77-96% respectively.

Figure 8A:
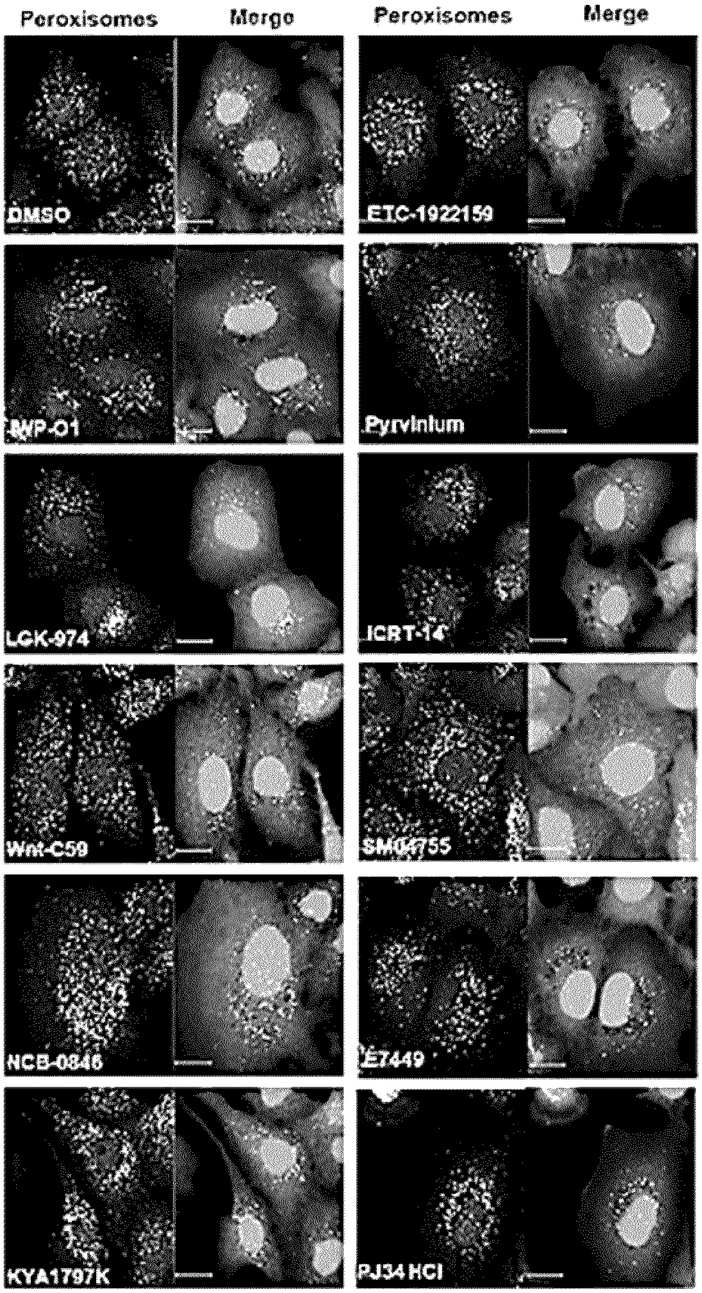
FIG. 8. Effect of Wnt/β-catenin inhibitors on peroxisomes. A549 cells were treated with the indicated drugs (1 mM for all except Pyrvinium (100 nm)) or DMSO alone for (A) 24 or (B) 48 hours before processing for confocal microscopy. Peroxisomes were detected with a rabbit polyclonal antibody to PEX14 and donkey anti-rabbit IgG conjugated to Alexa Fluor 546. Prior to mounting, samples were incubated with CellMask Deep Red. Images were obtained using a spinning-disc confocal microscope.
Figure 8B:
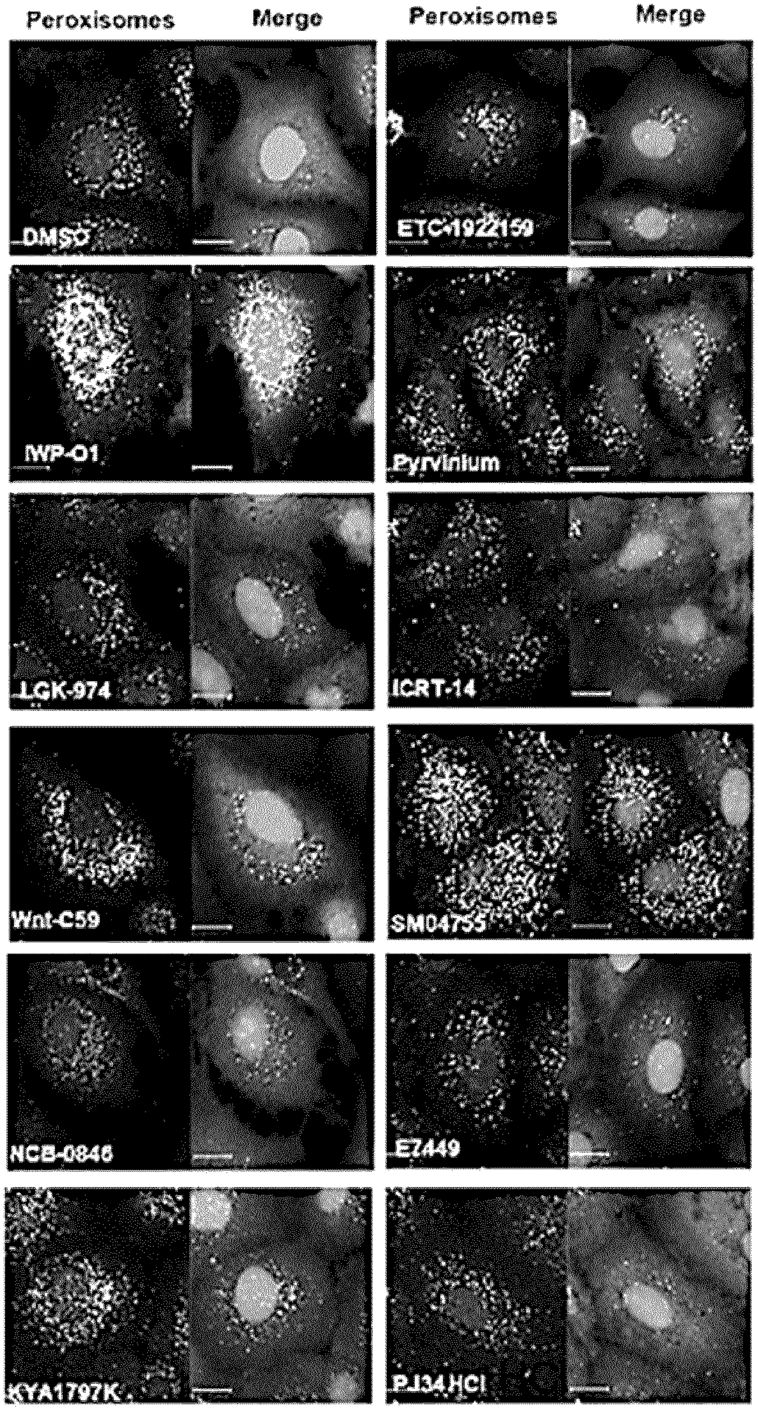
Figure 9:
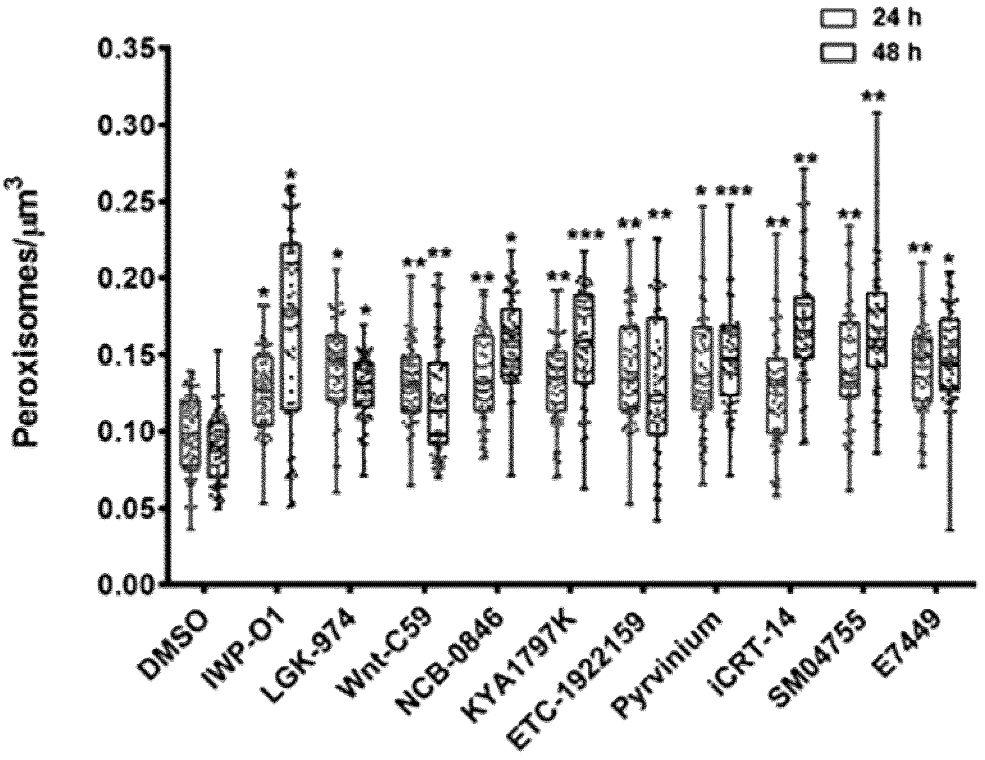
FIG. 9. Inhibitors of the Wnt/β-catenin pathway increase the density of peroxisomes in human cells. A549 cells were treated with DMSO alone or 10 different commercially available drugs (1 mM for all except Pyrvinium (100 nm)) that block Wnt/β-catenin signaling. Cells were fixed at 24- and 48-hours post-drug treatment and processed for confocal microscopy using an antibody against PEX14 to label peroxisomes and CellMask™ to label the plasma membrane. The numbers of peroxisomes in cell were determined using Volocity software. The peroxisome density (#/mm3) was calculated by dividing the number of peroxisomes by the estimated cell volume. For each sample, peroxisome densities in at least 10 cells were determined. Data from three independent experiments are shown. Error bars represent standard errors of the mean.

Wnt/β-Catenin Inhibitors Increase Peroxisome Density and Potentiate the Interferon Response While not wishing to be bound by theory, our underlying hypothesis for these studies was that Wnt/β-catenin inhibitors would inhibit virus replication by upregulating peroxisome biogenesis and subsequent interferon production. As a first step toward addressing this hypothesis, A549 cells were treated with the 10 Wnt/β-catenin inhibitors that had robust antiviral activity against SARS-CoV-2 or DMSO alone for 24 and/or 48 hours. Samples were then processed for quantitative confocal microscopy in order to determine how if/how the density of peroxisomes was affected by Wnt/β-catenin pathway inhibitors. A549 cells were chosen for these experiments as they have a morphology that is more amenable for quantitative analyses of organelles. Peroxisomes were identified using an antibody to PEX14, a peroxisome membrane protein involved in docking cargo-receptor complexes (reviewed in [6]). Samples were also incubated with a fluorescent dye that stains the entire cell in order to estimate cell volumes (FIG. 8). Each one of the drugs but not DMSO, significantly increased the density of peroxisomes at 24- and 48-hours post-treatment (FIG. 9); five of which (IWP-01, NCB-0846, KYA1979K, iCRT-14, and SM04755) increased peroxisome densities by more than 50%.

Figure 10A:
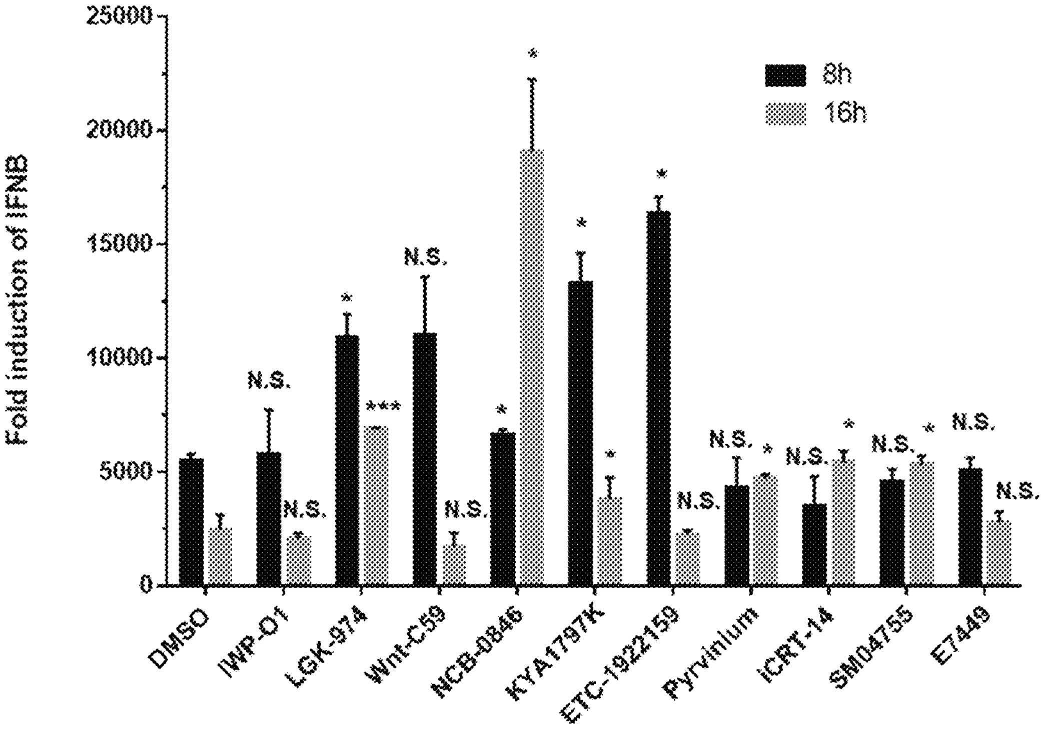
FIGS. 10A-10B. Wnt/β-catenin pathway inhibitors enhance production of type I and III interferons in response to viral infection. A549 cells were treated with DMSO alone or 10 different commercially available drugs (1 mM for all except Pyrvinium (100 nm)) that block Wnt/β-catenin signaling. Twenty-four hours later, cells were infected with Sendai virus (how much) for 8- or 16-hours after which total cellular RNA was harvested and subjected to qRT-PCR to determine relative levels mRNA encoding type I (IFNβ) and type III (IFNλ2) interferons. Values from three independent experiments are shown. Error bars represent standard errors of the mean.
Figure 10B:
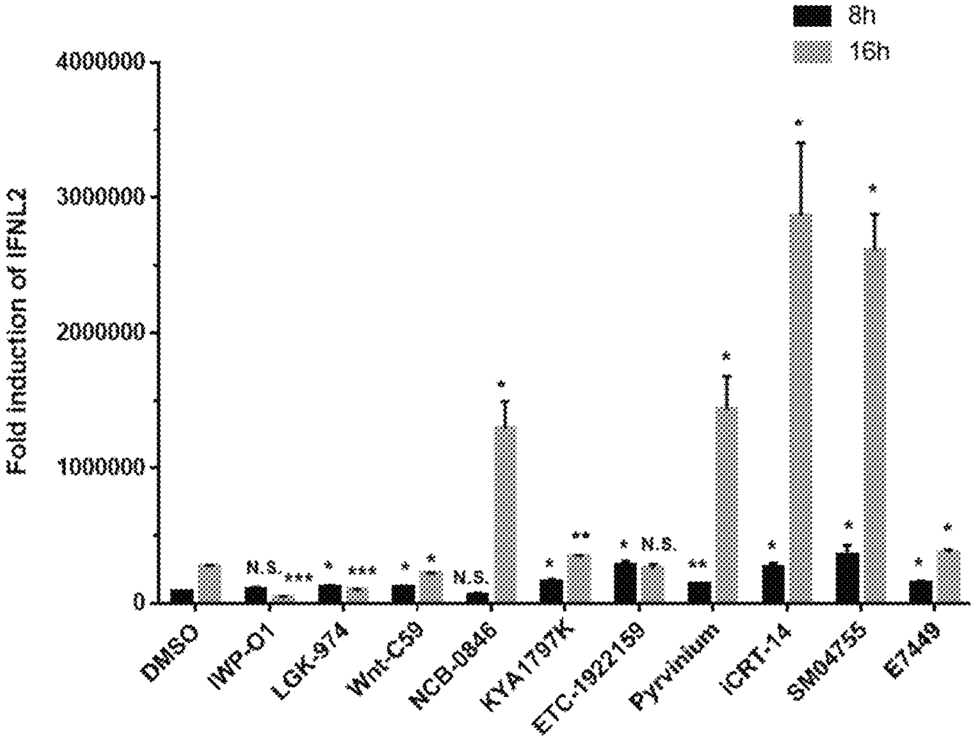
Figure 11:
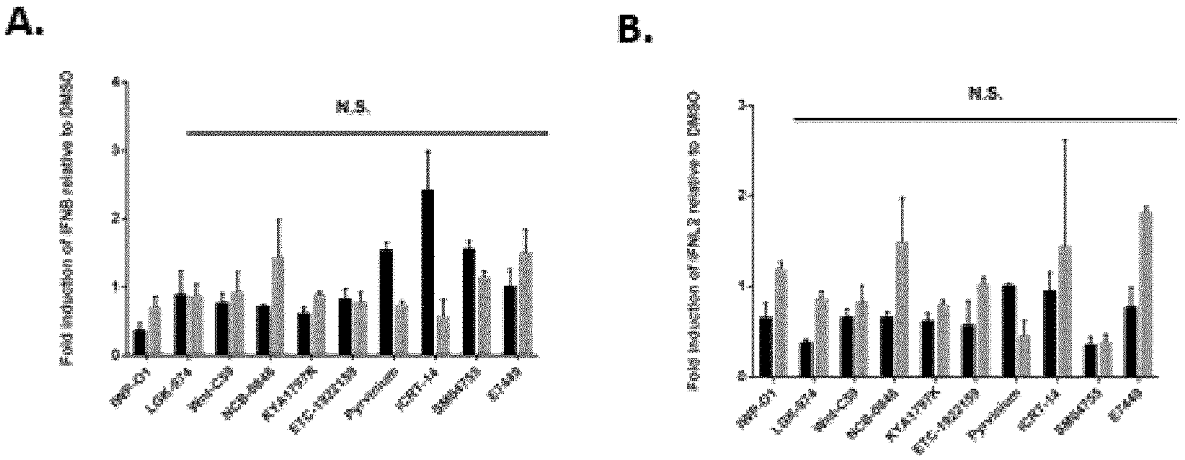
FIG. 11A-B. Wnt/β-catenin pathway inhibitors do not induce expression of interferon in the absence of viral infection. A549 cells were treated Wnt/β-catenin inhibitors (1 mM for all except Pyrvinium (100 nm)) or DMSO alone for 32- or 40-hours after which total RNA was extracted from cells. Relative levels of IFN and IFNλ2 were determined by RT-qPCR. The average levels of expression IFN and IFNλ2 transcripts (normalized to actin mRNA) from 3 independent experiments are shown. Error bars represent standard errors of the means. N.S. (not significant)

Next, we assessed whether pharmacological induction of peroxisomes by inhibiting the Wnt/β-catenin signaling pathway potentiated IFN production. A549 cells were treated with DMSO alone or Wnt/β-catenin inhibitors for 24-hours and then infected with Sendai virus, a potent inducer of the IFN response. Total RNA was harvested from cells for 8- and 16-hour post-infection and relative levels of IFN and IFNλ2 transcripts were determined by qRT-PCR. Data in FIG. 10 show that treatment with LGK-974, NCB-0846, KYA1797K, ETC-1922159, Pyrvinium and iCRT-14 significantly increased production of IFN in response to viral infection. While there was some overlap between drugs that potentiated type I and III IFN, the effects of some drugs (NCB-0846, Pyrvinium, iCRT-14 and SM04755) had much more dramatic effects on induction of type III IFN (FIG. 10). Wnt/β-catenin pathway inhibitors did not upregulate expression of IFN or IFNλ2 in the absence of viral infection (FIG. 11).

Figure 12:
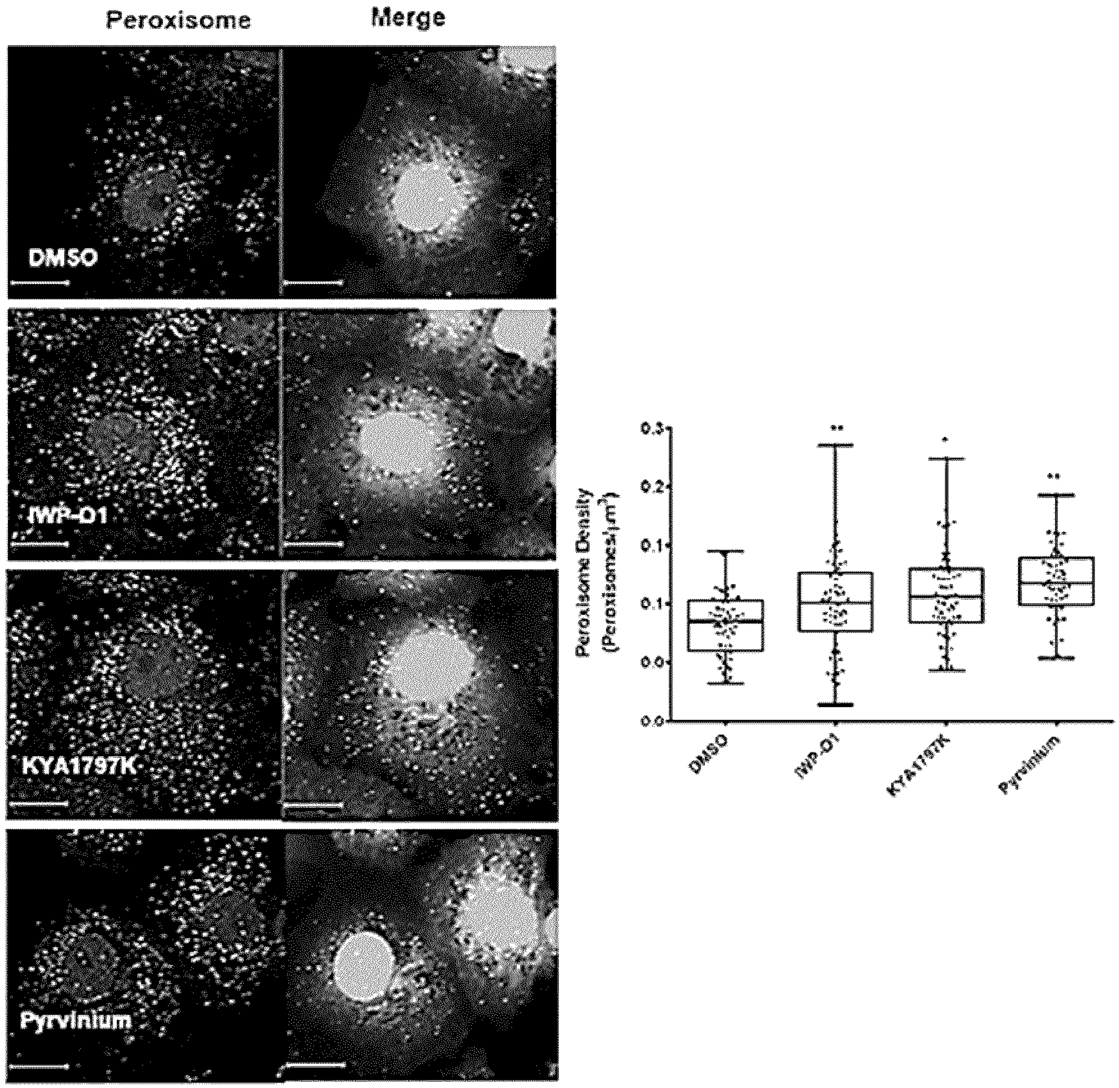
FIG. 12. Inhibition of the Wnt/β-catenin pathway increases peroxisome density in Vero cells. Vero cells were treated with DMSO alone or 1 μM IWP0O1, KYA17978K, or 100 nM Pyrvinium for 48 hours before processing for confocal microscopy. Peroxisomes were detected with a rabbit polyclonal antibody to PEX14 and donkey anti-rabbit IgG conjugated to Alexa Fluor 546. Prior to mounting, samples were incubated with CellMask Deep Red. Images were obtained using a spinning-disc confocal microscope. Box-and-whisker plot of the peroxisomal density in Vero cells are shown on the right. Peroxisomal density was calculated by quantifying the number of PEX14 puncta structures from Z-stack confocal images of the entire cell and dividing by the cell volume. Boxes show the 25th, 50th, and 75th percentiles. Points represent a minimum of 60 cells which were analyzed in three independent experiments. *, P<0.05; , P<0.01; *, P<0.001
Figure 13:
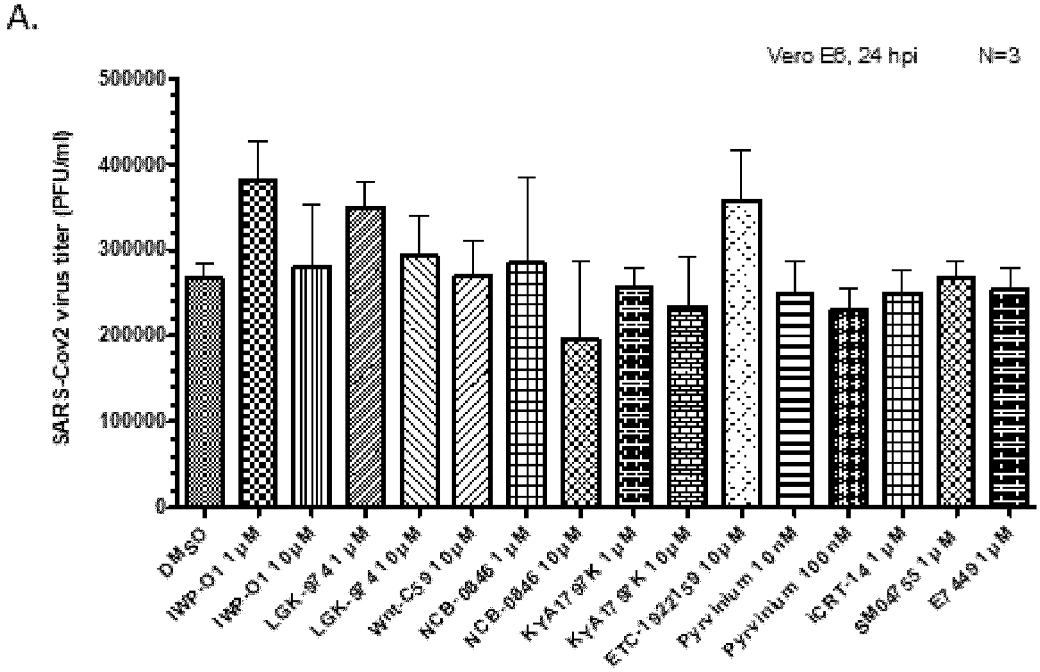
FIG. 13. Wnt/β-catenin inhibitors do not reduce SARS-CoV-2 replication in Vero cells. Vero E6 cells were pre-treated with Wnt inhibitors at indicated concentrations for 24 hours and then infected with SARS-CoV-2 (CANADA/VIDO01/2020 strain, MOI of 0.5). Twenty-four hours later, virus-containing media were subjected to plaque assays and total RNA extracted from cells was subjected to qRT-PCR to determine relative levels of viral RNA. Average viral titers (A) and genomic RNA levels (B) from drug-treated cells from 3 independent experiments are shown. Error bars represent standard error of the mean, *p<0.05.
Figure 13:
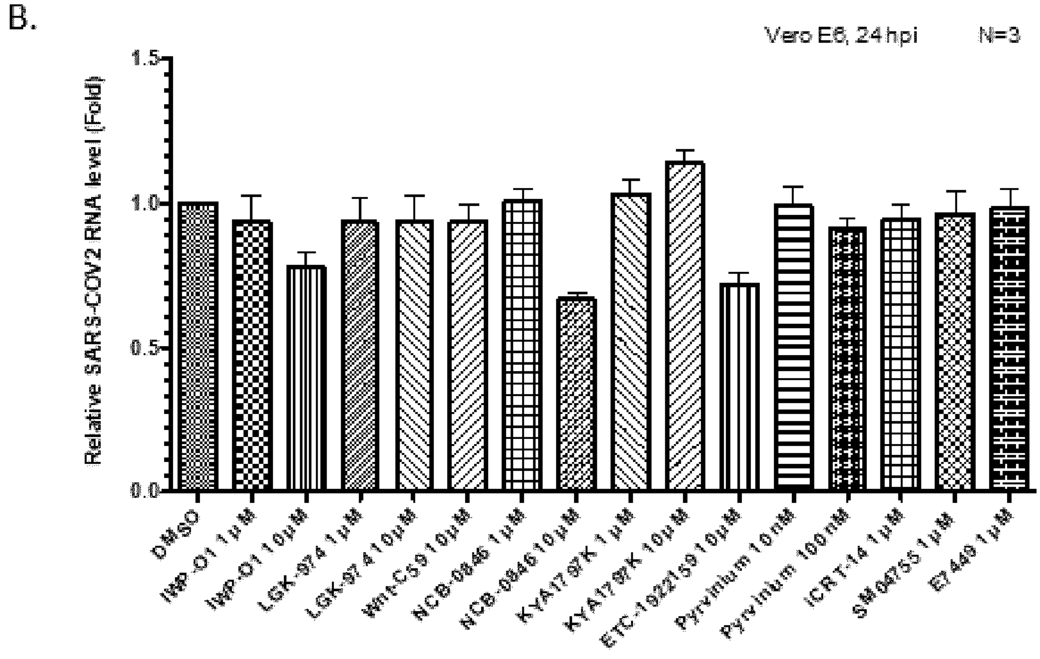

Together, the data presented above are consistent with a scenario in which Wnt/β-catenin inhibitors reduce SARS-CoV-2 replication because of an enhanced innate immune response that results from increased peroxisome density. To discern whether the antiviral activities of Wnt/β-catenin inhibitors on peroxisome biogenesis and IFN production could be unlinked, we tested their ability to inhibit SARS-CoV-2 replication in Vero cells, which do not produce type I IFN[7]. Similar to what was observed in A549 cells, treatment of Vero cells with three different Wnt/β-catenin inhibitors significantly increased the density of peroxisomes (FIG. 12). However, none of these drugs or seven other Wnt/β-catenin inhibitors were able to reduce replication of SARS-CoV-2 in Vero cells (FIG. 13). These results suggest that the antiviral effects of Wnt/β-catenin inhibitors are dependent upon the ability of treated cells to produce IFN.

Figure 7E:
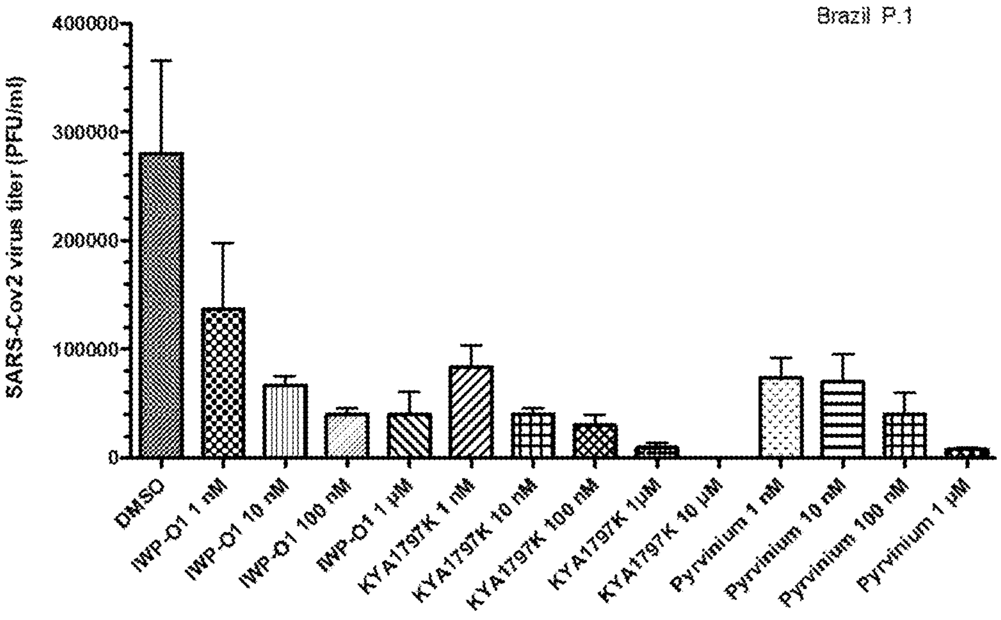
Figure 14:
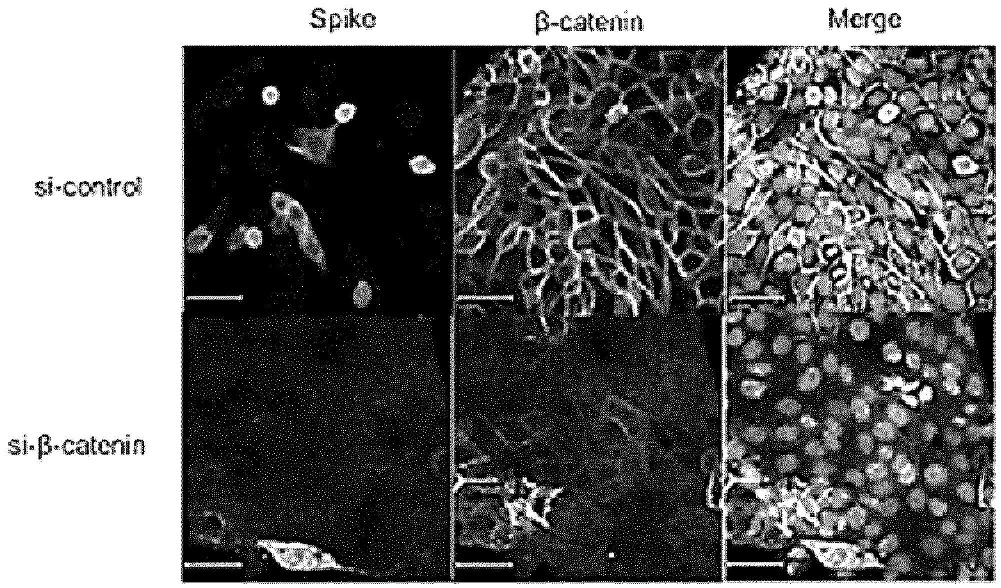
FIG. 14. Cells depleted of β-catenin are resistant to SARS-CoV-2 infection. Calu-3 cells were transfected with β-catenin-specific siRNAs or a non-targeting control siRNA for 48 hours. Cells were then processed for indirect immunofluorescence and confocal microscopy. Peroxisomes were detected with a rabbit polyclonal antibody to β-catenin, mouse polyclonal antibody to SARS-CoV-2 Spike protein, donkey anti-rabbit IgG conjugated to Alexa Fluor 546, and donkey mouse IgG conjugated to Alexa Fluor 488. Images were obtained using a spinning-disc confocal microscope.
Figure 15:
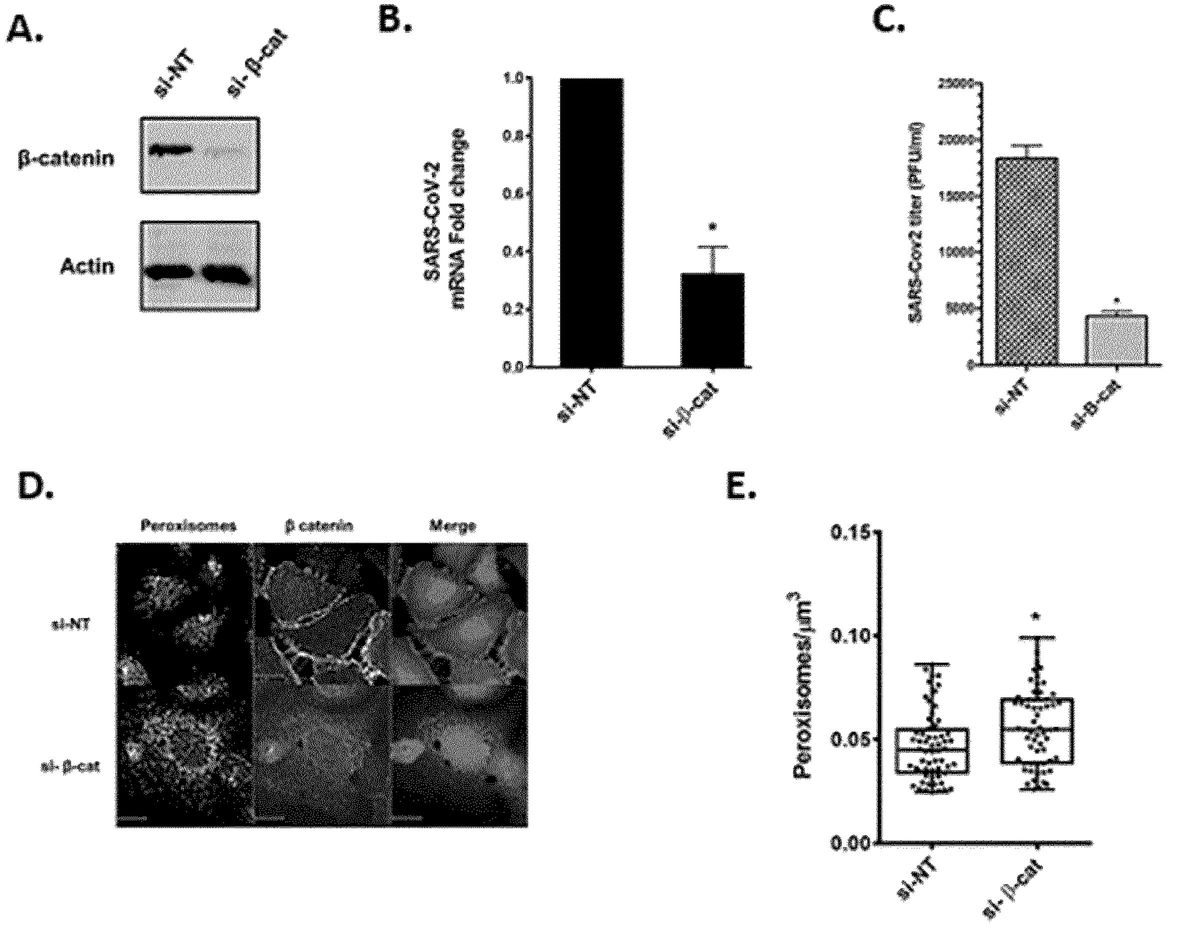
FIG. 15. Reducing β-catenin expression increases peroxisome density and inhibits replication of SARS-CoV-2. Calu-3 cells were transfected with siRNA against β-catenin or a control non-targeting siRNA for 48 hours after which cell lysates were processed for immunoblot analyses with antibodies to β-catenin and actin (A) or qRT-PCR to determine levels of viral genomic RNA relative to actin mRNA (B). Cell media were subjected to plaque assay to determine viral titers (C). The average levels of expression (normalized to actin) from 3 independent experiments were determined. Error bars represent standard errors of the means. D. A549 cells were transfected siRNA against β-catenin or a control non-targeting siRNA for 48 hours. Cells were then fixed and processed for indirect immunofluorescence and confocal microscopy. Peroxisomes were detected with a rabbit polyclonal antibody to PEX14 and donkey anti-rabbit IgG conjugated to Alexa Fluor 546. Prior to mounting, samples were incubated with CellMask Deep Red. Images were obtained using a spinning-disc confocal microscope. E. Box-and-whisker plot of the peroxisomal density of cells in. The peroxisomal densities were calculated by quantifying the number of PEX14 puncta structures from Z-stack confocal images of the entire cell and dividing by the cell volume. Boxes show the 25th, 50th, and 75th percentiles. Points represent a minimum of 60 cells which were analyzed in three independent experiments. *, P<0.05

Reducing β-Catenin Levels Induces Peroxisome Proliferation and Reduces SARS-CoV-2 Infection Activation of the canonical Wnt/β-catenin signaling pathway results in stabilization of the cytoplasmic pool of β-catenin followed by it's translocation into the nucleus where it functions with T cell factor/lymphoid enhancer factor transcription factors to drive expression of target genes that drive cell cycle progression and differentiation (reviewed in [8]). To determine if reducing the levels of β-catenin would have a similar effect on SARS-CoV-2 replication as Wnt/β-catenin signaling inhibitors, Calu-3 cells were transfected with siRNAs against β-catenin or a non-targeting siRNA for 48 hours. Cells were then infected with SARS-CoV-2 for 24 hours after which media and total cellular RNA were harvested for plaque assay and qRT-PCR respectively. Cells with reduced expression of β-catenin (FIG. 14) were less susceptible to infection by SARS-CoV-2 and as a result, levels of viral genomic RNA in these cells and viral titers in the culture media were significantly lower (FIGS. 15B and 15C). Reduction in β-catenin levels was also correlated with an increase in the peroxisome pool (FIGS. 15D and 7E). Together, these data suggest that β-catenin may downregulate antiviral signaling by suppressing peroxisome biogenesis.

Wnt/β-Catenin Inhibitors have Broad-Spectrum Antiviral Activity

Figure 16:
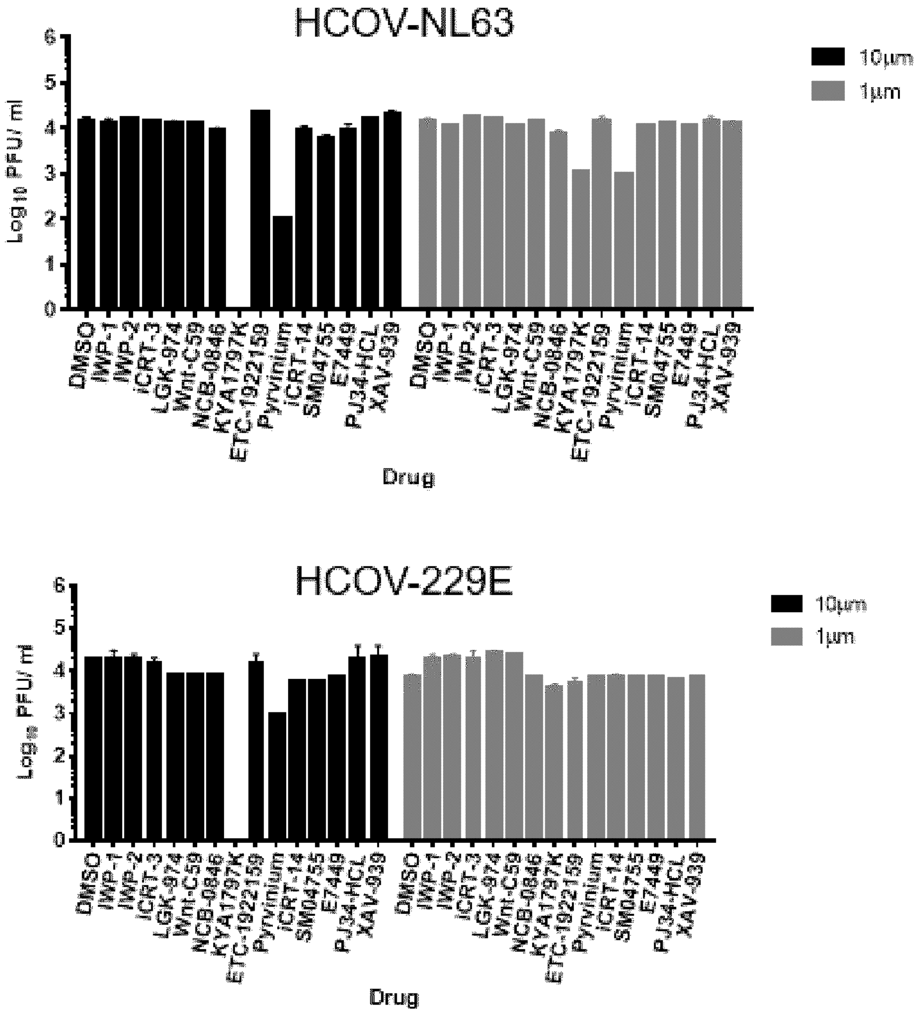
FIG. 16. Effect of Wnt/β-catenin inhibitors on other human coronaviruses (HCOVs). Calu3 cells were treated with the indicated concentrations of Wnt/β-catenin inhibitors for 24 hours and then infected with HCOVs NL63 or 229E MOI of 0.5). Twenty-four hours later, media were collected and subjected to plaque assay to determine viral titers. Average titers from there independent experiments are shown.
Figure 17B:
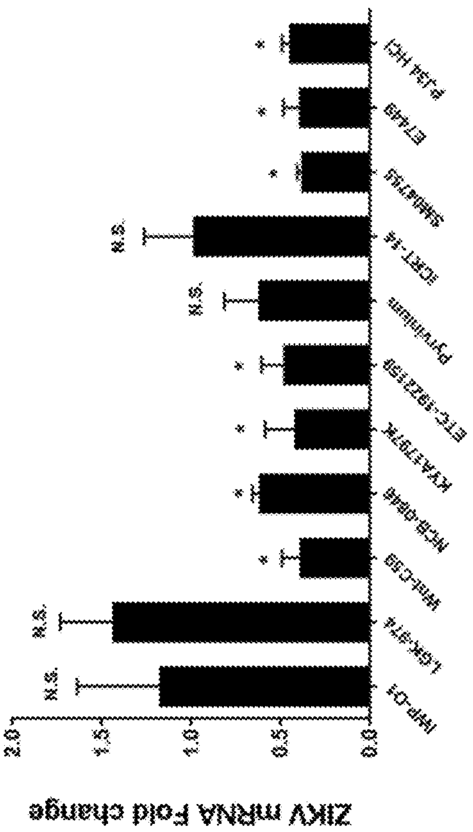
FIGS. 17A-17D. Wnt/β-catenin inhibitors reduce replication of other RNA viruses. A549 cells were treated with Wnt/β-catenin inhibitors (1 μM) or DMSO alone for 24 hours, after which the cells were infected with 0.1 MOI of Zika virus (ZIKV) or Mayaro virus (MAYV). Forty-eight hours later, virus-containing media were subjected to plaque assays and total RNA extracted from cells was subjected to qRT-PCR to determine relative levels of viral RNA. Average viral titers (FIG. 17A, FIG. 17C) and genomic RNA levels (FIG. 17B, FIG. 17D) from drug-treated cells from 3 independent experiments are shown. Error bars represent standard error of the mean. *, P<0.05; **, P<0.01; N.S. (not significant).
Figure 17A:
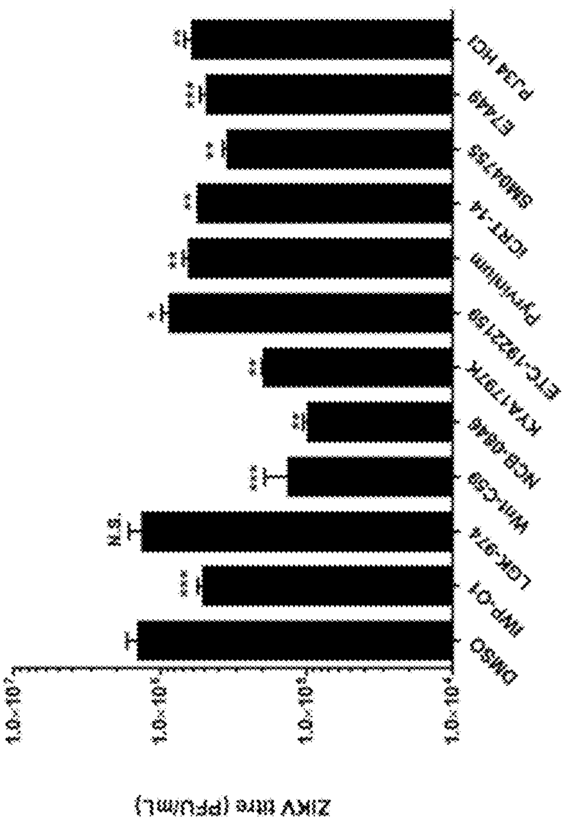
Figure 17D:
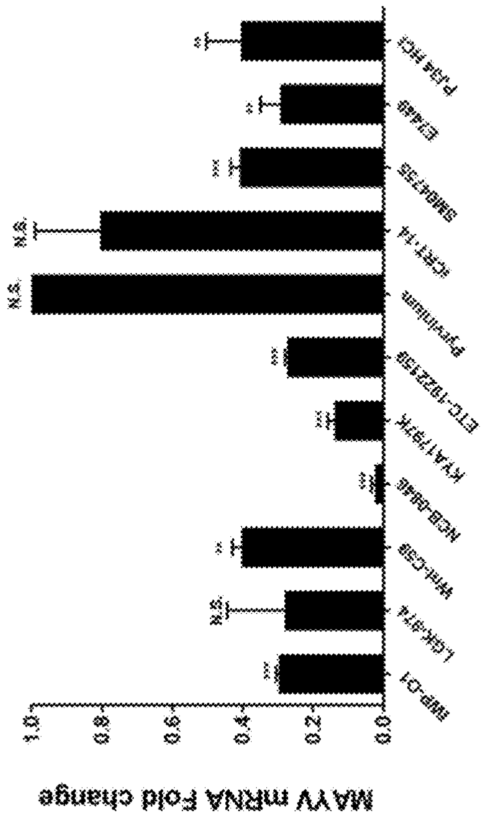
Figure 17C:
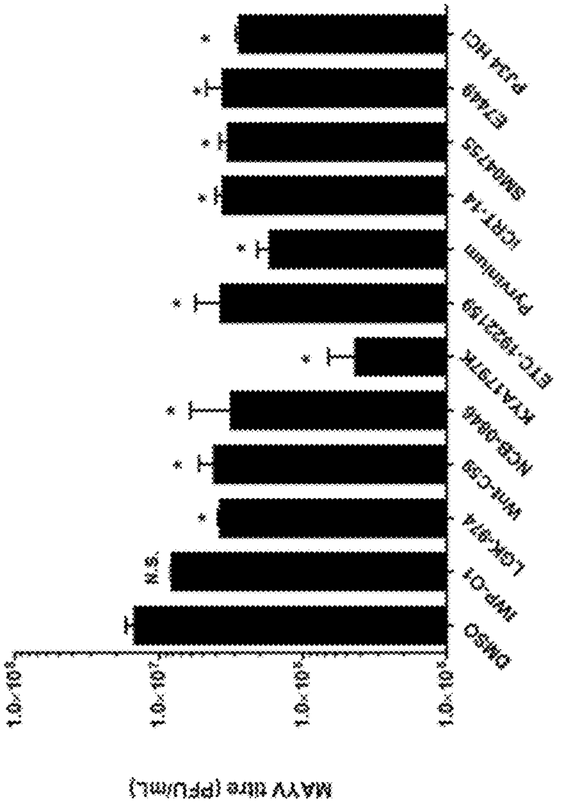
Figure 18:
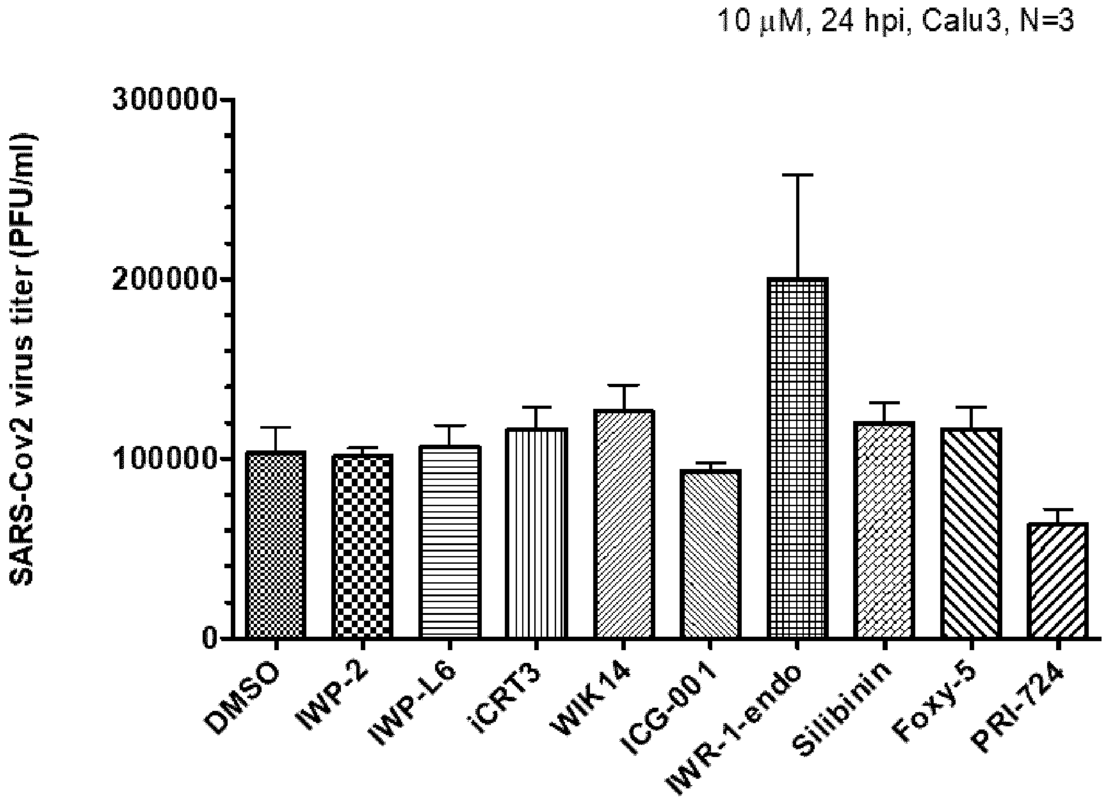
FIG. 18 depicts Calu-3 cells were treated with the indicated concentrations of drugs or DMSO for 24 hours before infection with SARS-CoV-2 (MOI=0.5). Media were harvested 24 hours later and viral titers were determined by plaque assay.
Figure 19:
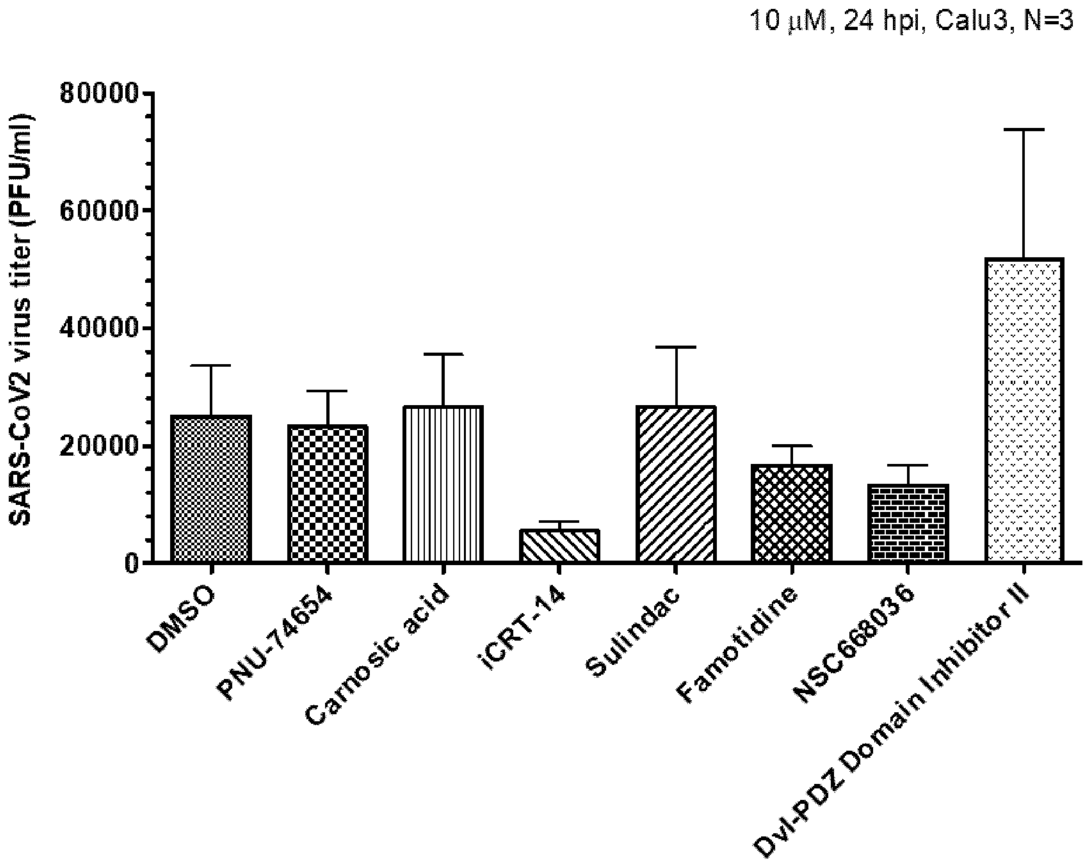
FIG. 19 depicts Calu-3 cells were treated with the indicated concentrations of drugs or DMSO for 24 hours before infection with SARS-CoV-2 (MOI=0.5). Media were harvested 24 hours later and viral titers were determined by plaque assay.
Figure 20:
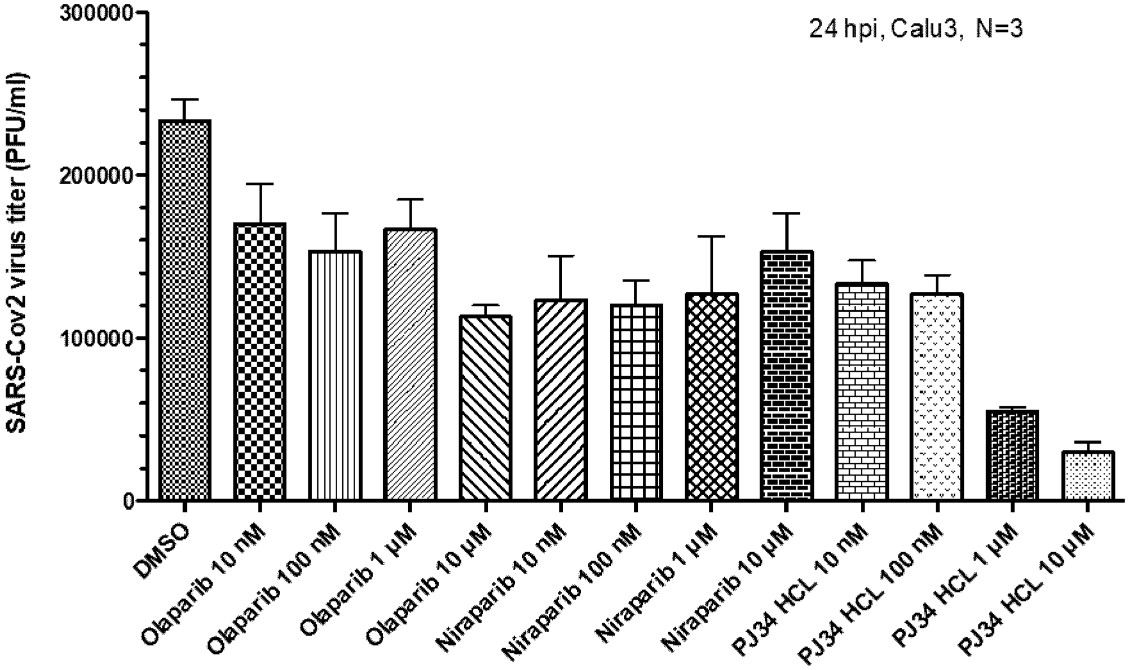
FIG. 20 depicts Calu-3 cells were treated with the indicated concentrations of drugs or DMSO for 24 hours before infection with SARS-CoV-2 (MOI=0.5). Media were harvested 24 hours later and viral titers were determined by plaque assay.
Figure 21:
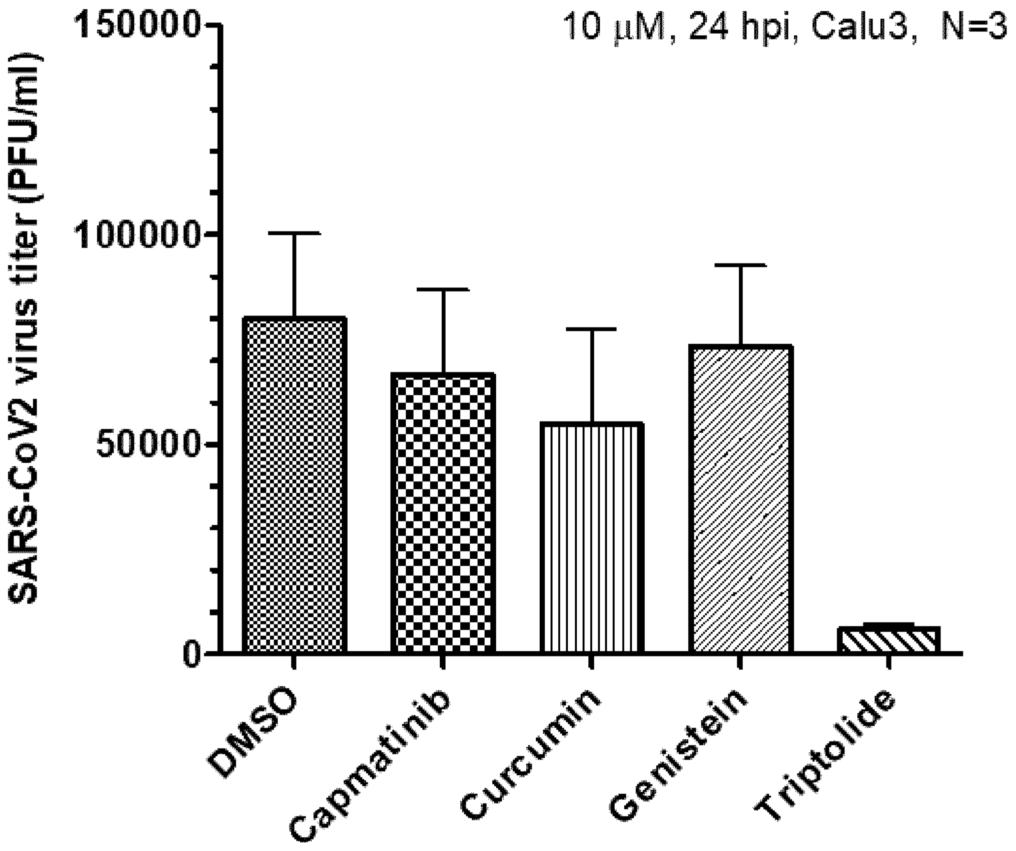
FIG. 21 depicts Calu-3 cells were treated with the indicated concentrations of drugs or DMSO for 24 hours before infection with SARS-CoV-2 (MOI=0.5). Media were harvested 24 hours later and viral titers were determined by plaque assay.

Because Wnt/β-catenin inhibitors enhance the IFN response, we hypothesized that these drugs would be effective against other human coronaviruses and potentially other pathogenic RNA viruses such as flaviviruses and alphaviruses. To test this theory, Calu-3 and A549 cells treated with Wnt/β-catenin inhibitors or DMSO for 24 hours were infected with two different seasonal human coronavirus HCOV-NL63 and HCOV-229E for 24 hours or Zika virus or Mayaro virus for 48 and 24 hours respectively. Data in FIG. 16 show while most drugs did not have any significant effect, KYA1797K and to a lesser extent Pyrvinium significantly reduced titers of HCOV-NL63 and HCOV-229E. Similarly, KYA1797K was most potent against Zika virus and Mayaro virus but importantly, a number of drugs significantly reduced replication of these arboviruses (FIG. 17).

In FIGS. 18-21 Calu-3 cells were treated with the indicated concentrations of drugs or DMSO for 24 hours before infection with SARS-CoV-2 (MOI=0.5). Media were harvested 24 hours later and viral titers were determined by plaque assay.

REFERENCES

1. Dixit E, Boulant S, Zhang Y, et al. Peroxisomes are signaling platforms for antiviral innate immunity. Cell. 2010; 141(4):668-681.
2. Odendall C, Dixit E, Stavru F, et al. Diverse intracellular pathogens activate type III interferon expression from peroxisomes. Nat Immunol. 2014; 15(8):717-726.
3. Wong C P, Xu Z, Power C, Hobman T C. Targeted Elimination of Peroxisomes During Viral Infection: Lessons from HIV and Other Viruses. DNA Cell Biol. 2018; 37(5):417-421.
4. Wong C P, Xu Z, Hou S, et al. Interplay between Zika Virus and Peroxisomes during Infection. Cells. 2019; 8(7).
5. Xu Z, Lodge R, Power C, Cohen E A, Hobman T C. The HIV-1 Accessory Protein Vpu Downregulates Peroxisome Biogenesis. mBio. 2020; 11(2).
6. Fujiki Y, Abe Y, Imoto Y, et al. Recent insights into peroxisome biogenesis and associated diseases. J Cell Sci. 2020; 133(9).
7. Desmyter J, Melnick J L, Rawls W E. Defectiveness of interferon production and of rubella virus interference in a line of African green monkey kidney cells (Vero). J Virol. 1968; 2(10):955-961.
8. Albrecht L V, Tejeda-Munoz N, De Robertis E M. Cell Biology of Canonical Wnt Signaling. Annu Rev Cell Dev Biol. 2021.

Example 2

Drugs that inhibit different components of the Wnt signaling pathway potently reduce replication of SARS-CoV-2 in human lung epithelial cells (of continuous and primary origin).

Figure 22:
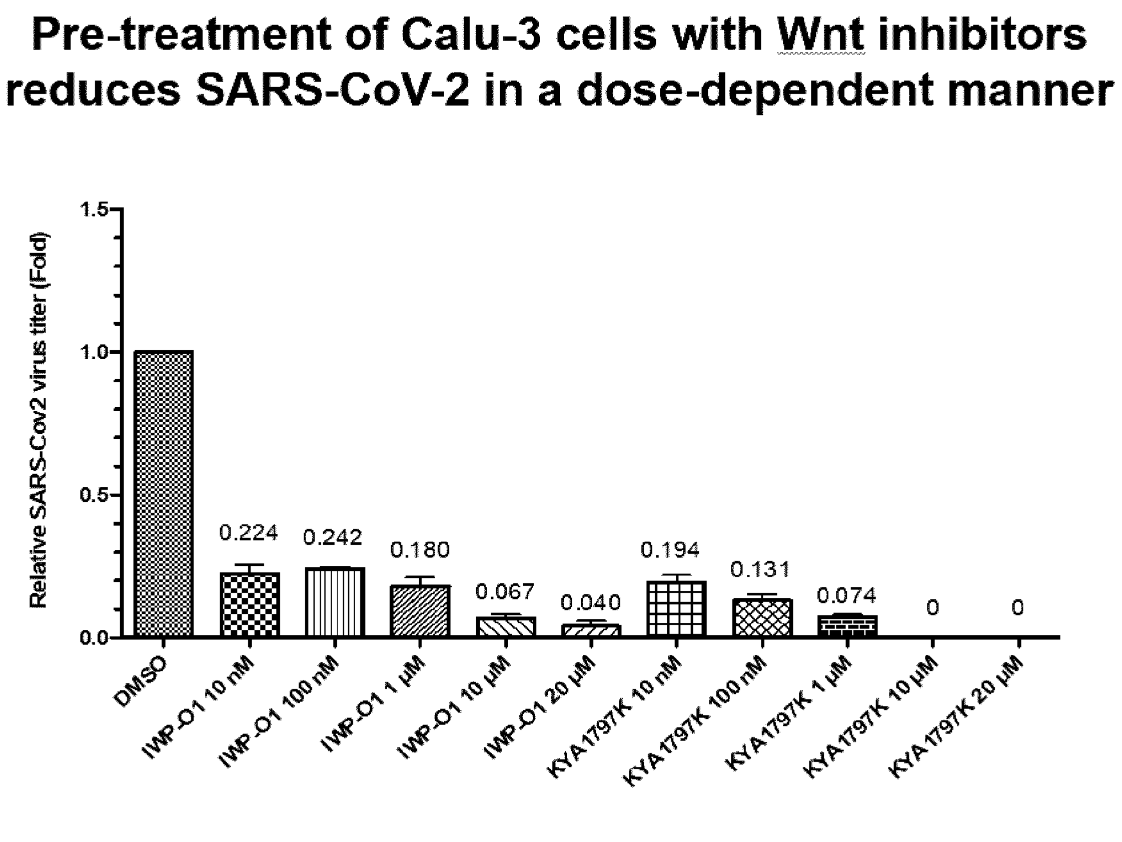
FIG. 22 depicts Pre-treatment of Calu-3 cells with Wnt inhibitors reduces SARS-CoV-2 in a dose-dependent manner

FIG. 22 depicts Pre-treatment of Calu-3 cells with Wnt inhibitors reduces SARS-CoV-2 in a dose-dependent manner Calu3 cells were pre-treated with the indicated concentrations of Wnt inhibitors IWP01 or KYA1797K (10 nM to 20 μM for 24 hours and then infected with SARS-CoV-2 (CANADA/VIDO01/2020 strain) using MOI of 0.5. Twenty-four hours later, cell media were collected and subjected to plaque assays to determine viral titers. Relative average viral titers from 3 independent experiments are shown. Error bars represent standard error of the mean, *p<0.05.

Figure 23:
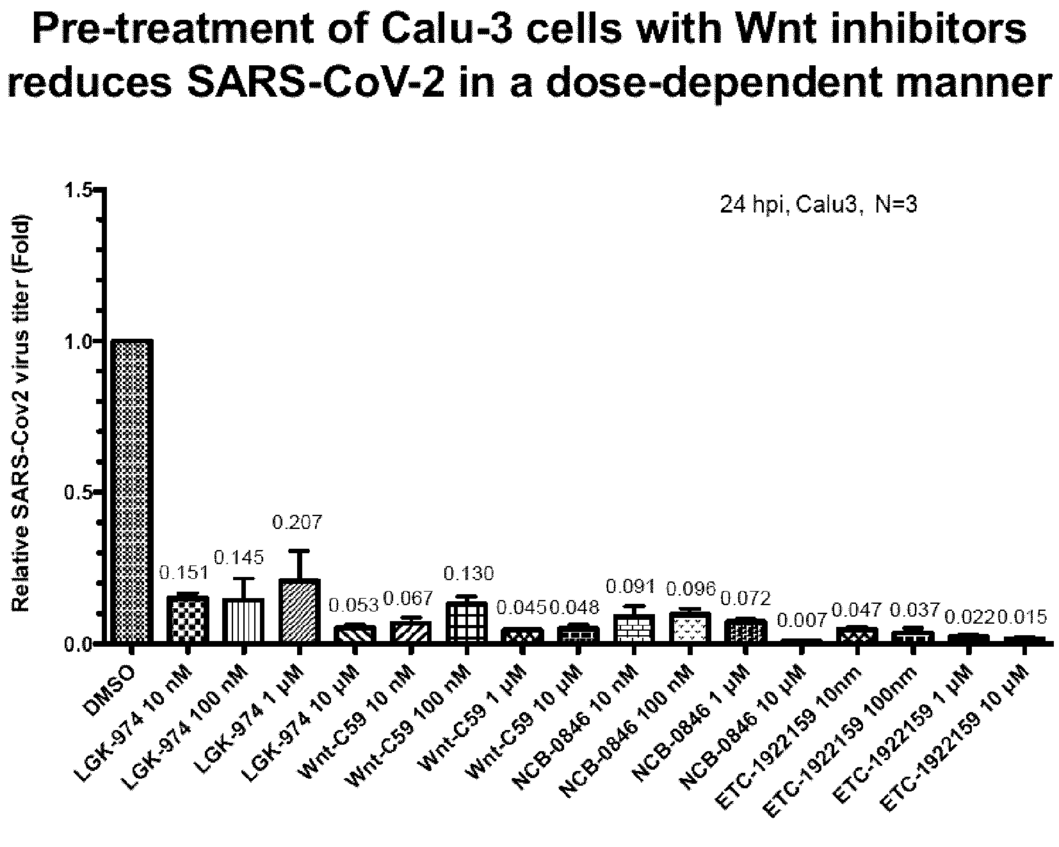
FIG. 23 depicts Pre-treatment of Calu-3 cells with Wnt inhibitors reduces SARS-CoV-2 in a dose-dependent manner.

FIG. 23 depicts Pre-treatment of Calu-3 cells with Wnt inhibitors reduces SARS-CoV-2 in a dose-dependent manner.

Calu3 cells were pre-treated with the indicated concentrations of Wnt inhibitors LGK-974, Wnt-C59, NCB-0846 or ETC-1922159 (10 nM to 10 μM for 24 hours and then infected with SARS-CoV-2 (CANADA/VIDO01/2020 strain) using MOI of 0.5. Twenty-four hours later, cell media were collected and subjected to plaque assays to determine viral titers. Relative average viral titers from 3 independent experiments are shown. Error bars represent standard error of the mean, *p<0.05.

Figure 24:
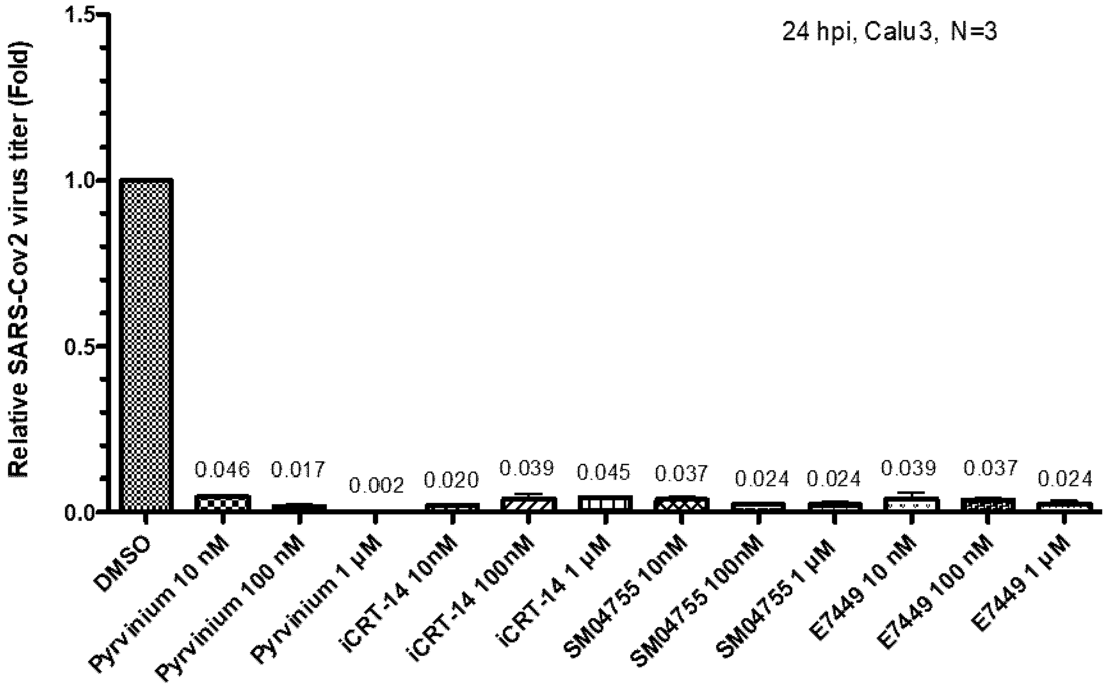
FIG. 24 depicts Pre-treatment of Calu-3 cells with Wnt inhibitors reduces SARS-CoV-2 in a dose-dependent manner.

FIG. 24 depicts Pre-treatment of Calu-3 cells with Wnt inhibitors reduces SARS-CoV-2 in a dose-dependent manner.

Calu3 cells were pre-treated with the indicated concentrations of Wnt inhibitors Pyrvinium, iCRT-14, SM04755 or E7449 (10 nM to 1 μM for 24 hours and then infected with SARS-CoV-2 (CANADA/VIDO01/2020 strain) using MOI of 0.5. Twenty-four hours later, cell media were collected and subjected to plaque assays to determine viral titers. Relative average viral titers from 3 independent experiments are shown. Error bars represent standard error of the mean, *p<0.05.

Figure 25:
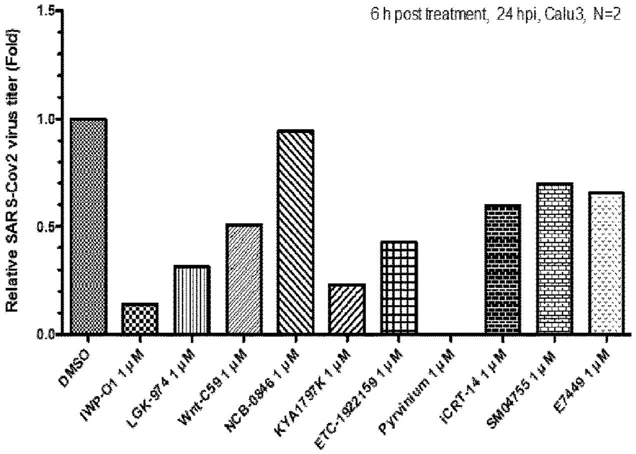
FIG. 25 depicts Wnt inhibitors reduce replication of SARS-CoV-2 in a dose-dependent manner when added to Calu-3 cells post-infection.

FIG. 25 depicts Wnt inhibitors reduce replication of SARS-CoV-2 when added to Calu-3 cells post-infection.

Calu3 cells were infected with SARS-CoV-2 (CANADA/VIDO01/2020 strain, MOI of 0.5) for 6-hours after which IWP01, LGK-974, Wnt-C59, NCB-0846, ETC-1922159, Pyrvinium, iCRT-14, SM04755, or E7449 were added to cells for 24 hours. Twenty-four hours after adding drugs, cell media were harvested and viral titers were determined by plaque assay. Relative viral titers are shown.

Figure 26:
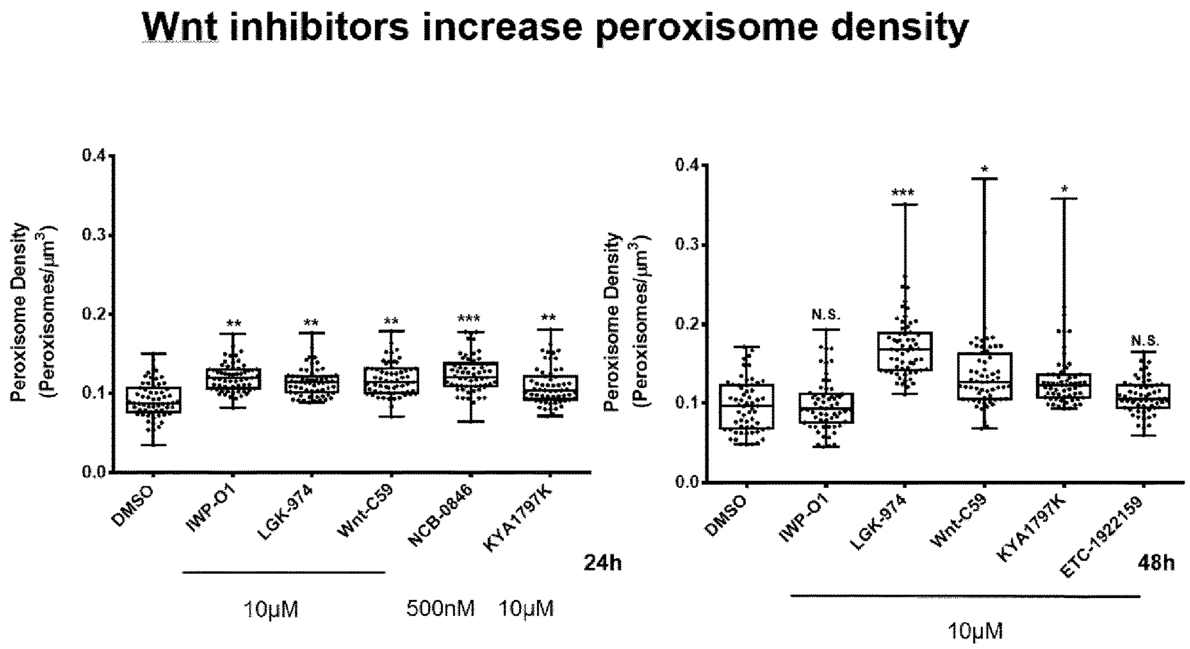
FIG. 26 depicts Wnt inhibitors increase peroxisome density.

FIG. 26 depicts Wnt inhibitors increase peroxisome density.

A549 cells were treated with DMSO alone, IWP-01, LGK-974, Wnt-C59, NCB-0846 or KYA1797K at the indicated concentrations. Cells were fixed at 24- and 48-hours post-drug treatment and processed for confocal microscopy using an antibody against PEX14 to label peroxisomes and CellMask™ to label the plasma membrane. The numbers of peroxisomes in cell were determined using Volocity software. The peroxisome density (#/μm$^3$) was calculated by quantifying the number of PEX14 puncta structures from Z-stack confocal images of the entire cell and dividing by the cell volume. Box-and-whisker plot of the peroxisome density in A549 cells is shown. Boxes show the 25th, 50th, and 75th percentiles. Points represent a minimum of 60 cells which were analyzed in three independent experiments. *, P<0.05; , P<0.01; *, P<0.001

Figure 27:
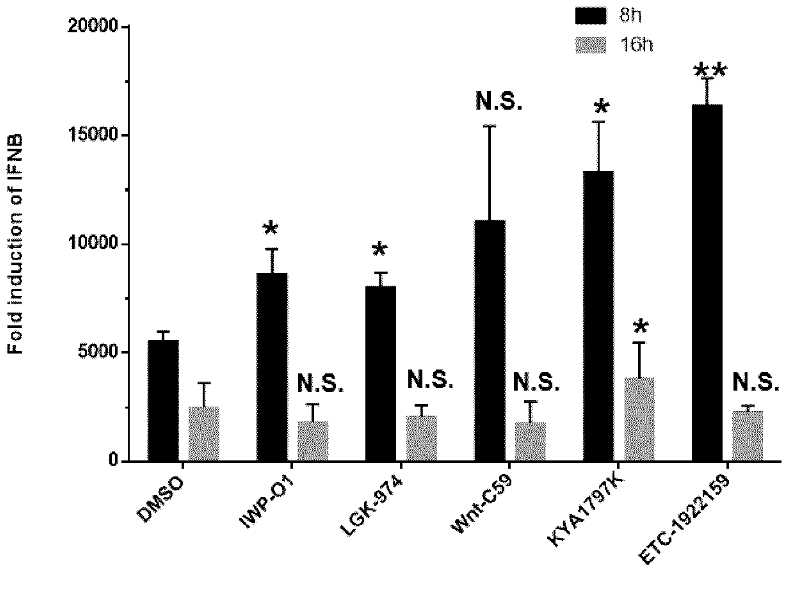
FIG. 27 depicts Wnt inhibitors enhance IFNβ expression in response to Sendai virus infection.

FIG. 27 depicts some Wnt inhibitors enhance IFNβ expression in response to Sendai virus infection.

A549 cells were treated with DMSO alone, IWP-O1, LGK-974, Wnt-C59, KYA1979K, or ETC-1922159 (1 μM each). Twenty-four hours later, cells were challenged with 100 HAU/ml of Sendai for 8- or 16-hours after which total cellular RNA was harvested and subjected to qRT-PCR to determine relative levels mRNA encoding IFN Values from three independent experiments are shown. Error bars represent standard errors of the mean. *, P<0.05; **, P<0.01; N.S. (not significant)

Figure 28:
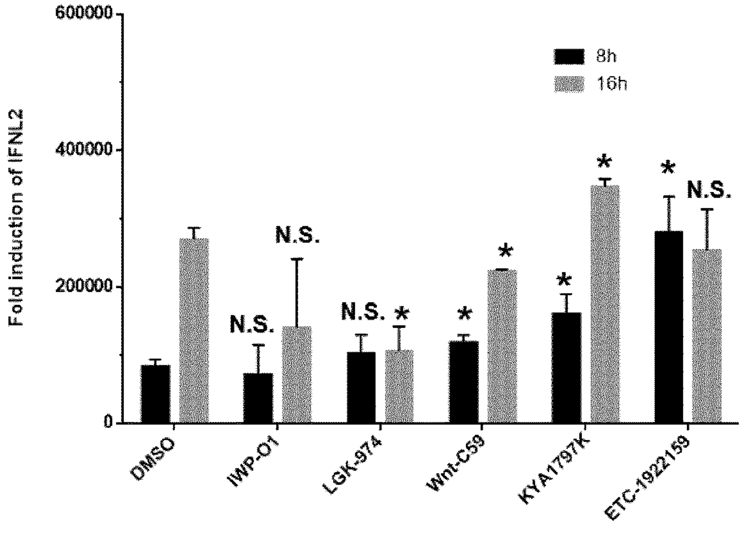
FIG. 28 depicts Some Wnt inhibitors enhance IFNλ expression in response to Sendai virus infection.

FIG. 28 depicts Some Wnt inhibitors enhance IFNλ expression in response to Sendai virus infection.

A549 cells were treated with DMSO alone, IWP-O1, LGK-974, Wnt-C59, KYA1979K, or ETC-1922159 (1 μM each). Twenty-four hours later, cells were challenged with 100 HAU/ml of Sendai for 8- or 16-hours after which total cellular RNA was harvested and subjected to qRT-PCR to determine relative levels mRNA encoding IFNλ2 Values from three independent experiments are shown. Error bars represent standard errors of the mean. *, P<0.05; N.S. (not significant)

Figure 29:
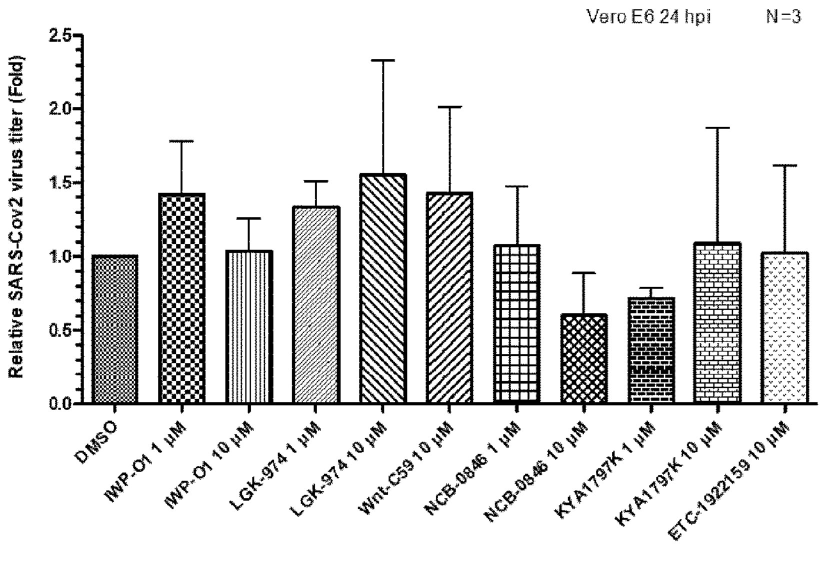
FIG. 29 depicts Pre-treatment of Vero cells with Wnt inhibitors does not significantly reduce SARS-CoV-2 replication.

FIG. 29 depicts Pre-treatment of Vero cells with Wnt inhibitors does not significantly reduce SARS-CoV-2 replication.

Vero E6 cells were pre-treated with Wnt inhibitors at indicated concentrations for 24 hours and then infected with SARS-CoV-2 (CANADA/VIDO01/2020 strain, MOI of 0.5). Twenty-four hours later, virus-containing media were subjected to plaque assays. Average viral titers from 3 independent experiments are shown. Error bars represent standard error of the mean.

Figure 30:
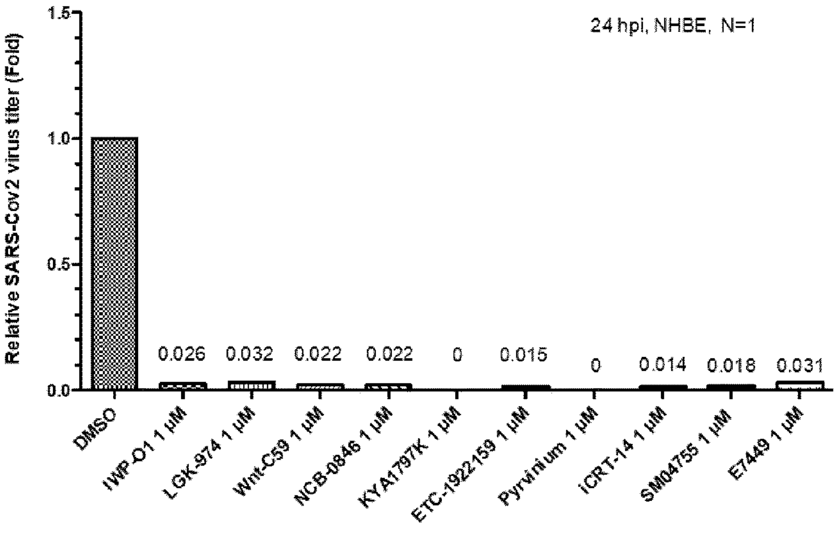
FIG. 30 depicts Pre-treatment of Normal Human Bronchial Epithelial cells with Wnt inhibitors reduces replication of SARS-CoV-2.

FIG. 30 depicts Pre-treatment of Normal Human Bronchial Epithelial cells with Wnt inhibitors reduces replication of SARS-CoV-2.

Primary human NHBE cells were pre-treated with Wnt inhibitors at indicated concentrations for 24 hours and then infected with SARS-CoV-2 (CANADA/VIDO01/2020 strain) using MOI of 0.5 for 24 hours. Virus-containing media were then subjected to plaque assay to determine viral titers. Relative viral titers are shown.

Wnt inhibitors work best when added to cells before infection starts but Pyrvinium, IWP-01, LGK-974 and KYA1797K effectively block SARS-CoV-2 replication when added 6-hours post-infection.

Wnt inhibitors induce peroxisome proliferation and interferon production in response to viral infection.

Wnt inhibitors are not effective in Vero cells.

Suggests that antiviral mechanism of action requires type I interferon.

These results suggest the use of Wnt inhibitor in prophylaxis and/or early stage treatment of COVID-19 patients.

Most promising candidates: Pyrvinium, KYA1797K, IWP-O1, LGK-974, Wnt-C59, iCRT-14, SM04755, E7449, ETC-1922159, NCB-0846.

Example 3

Figure 31:
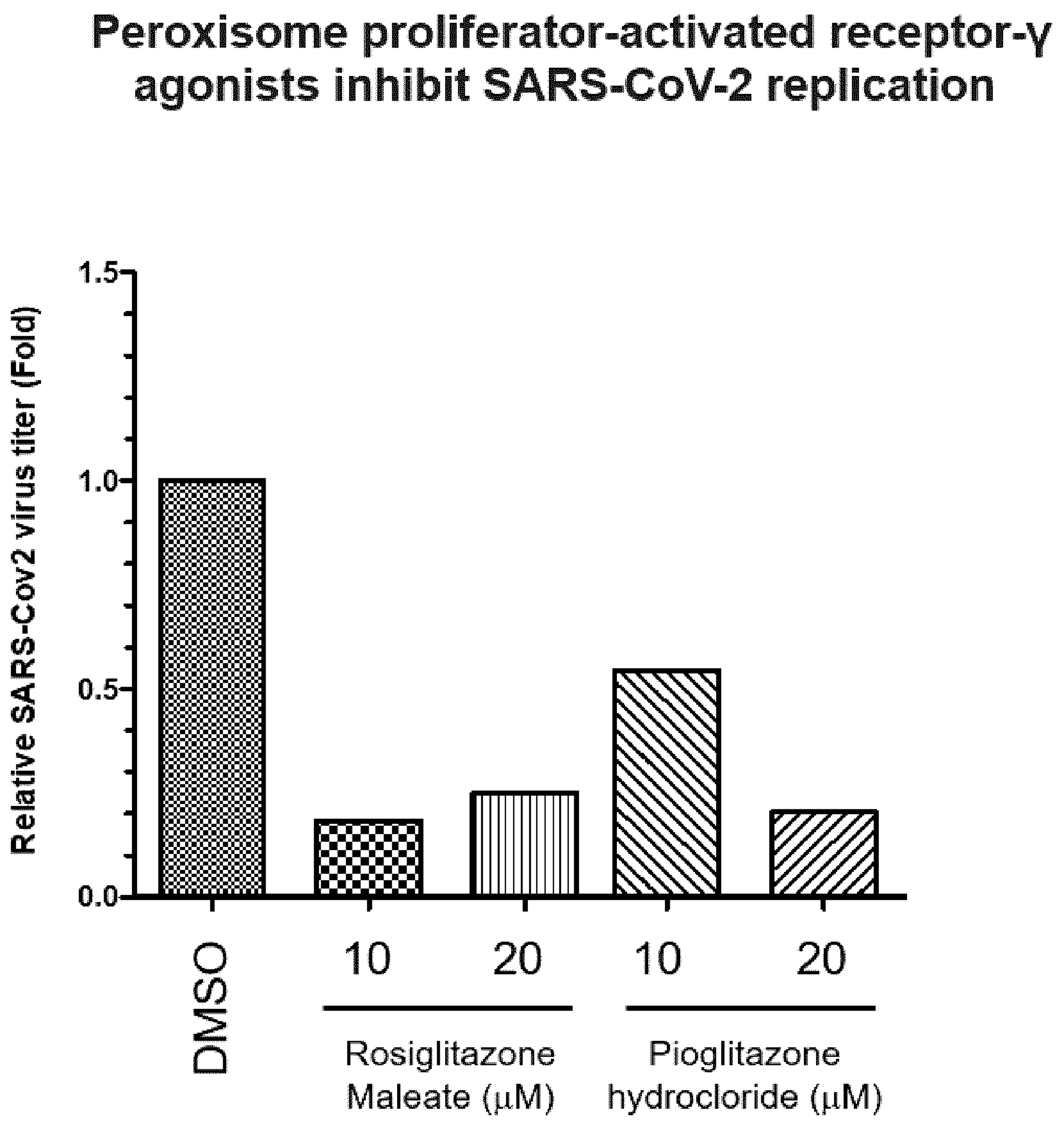
FIG. 31 depicts Peroxisome proliferator-activated receptor-y agonists inhibit SARS-CoV-2 replication. Calu-3 cells were pretreated with DMSO alone or the indicated concentrations of peroxisome proliferator-activated receptor-y agonists for 24 hours followed by infection with SARS-CoV-2 (MOI=0.5) for 24 hours. Cell media were harvested for plaque assays and relative viral titers are shown.

FIG. 31 shows that PPAR gamma agonists (Rosiglitazone Maleate and Pioglitazone hydrochloride) inhibit SARS-CoV-2 replication.

Method: Calu-3 cells were pretreated with DMSO alone or the indicated concentrations of peroxisome proliferator-activated receptor-γ agonists for 24 hours followed by infection with SARS-CoV-2 (MOI=0.5) for 24 hours. Cell media were harvested for plaque assays and relative viral titers are shown.

In other examples, the PPAR gamma agonists may include Lobeglitazone, chiglitazar, KDT-501, Navaglitazar, AVE-0897, ZY-H2, AMG-131, Muraglitazar, Amorfrutins, Formonetin, Bixin, Norbixin, Commipheric acid, Citral, Meranzin, Carnosic acid, Carnosol, Linoleic acid, Saurufuran, Isosilybin A, Gallotannins, or Carvacrol.

FIG. 31 depicts Peroxisome proliferator-activated receptor-γ agonists inhibit SARS-CoV-2 replication. Calu-3 cells were pretreated with DMSO alone or the indicated concentrations of peroxisome proliferator-activated receptor-γ agonists for 24 hours followed by infection with SARS-CoV-2 (MOI=0.5) for 24 hours. Cell media were harvested for plaque assays and relative viral titers are shown.

Figure 32:
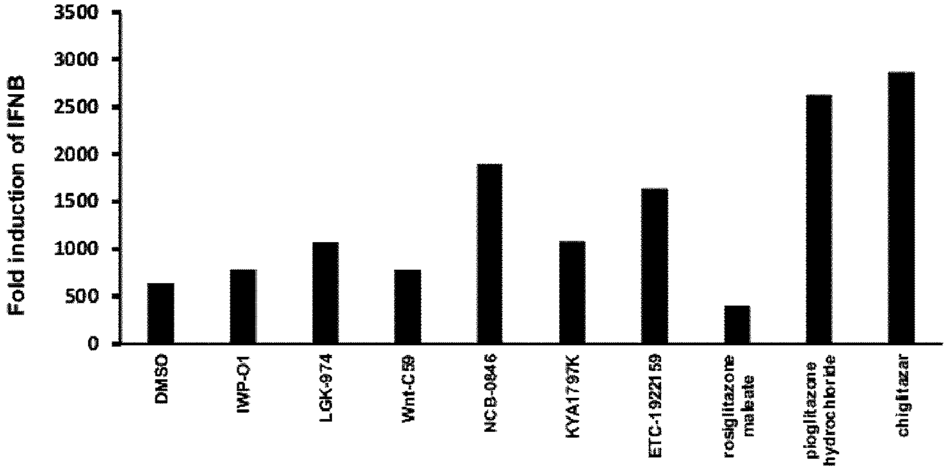
FIG. 32 depicts fold induction of IFNβ at 16 hr post infection of Sendai virus in A549 cellstreated with Wnt inhibitors/PPAR agonists. A549 cells were treated with DMSO alone, Wnt inhibitors at 1 micromolar (IWP-O1, LGK-974, Wnt-C59, NCB-0846, KYA1979K, or ETC-1922159) or PPAR gamma agonists at 10 micromolar (Pioglitazone hydrochloride and chiglitazar). Twenty-four hours later, cells were challenged with 100 HAU/ml of Sendai for 16-hours after which total cellular RNA was harvested and subjected to qRT-PCR to determine relative levels of mRNA encoding IFNβ. Values from two independent experiments are shown.

FIG. 32 depicts fold induction of IFN at 16 hr post infection of Sendai virus in A549 cells treated with Wnt inhibitors/PPAR agonists. A549 cells were treated with DMSO alone, Wnt inhibitors at 1 micromolar (IWP-O1, LGK-974, Wnt-C59, NCB-0846, KYA1979K, or ETC-1922159) or PPAR gamma agonists at 10 micromolar (Pioglitazone hydrochloride and chiglitazar). Twenty-four hours later, cells were challenged with 100 HAU/ml of Sendai for 16-hours after which total cellular RNA was harvested and subjected to qRT-PCR to determine relative levels of mRNA encoding IFNβ. Values from two independent experiments are shown.

In other example, the PPAR alpha agonist may include Fenofibrate, ciprofibrate, clofibrate, gemfibrozil, bezafibrate, or Elafibranor.

The embodiments described herein are intended to be examples only. Alterations, modifications and variations can be effected to the particular embodiments by those of skill in the art. The scope of the claims should not be limited by the particular embodiments set forth herein but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A method of treating a subject infected with SARS-CoV-2, suspected of being infected with SARS-CoV-2, or at risk of being infected with SARS-CoV-2, comprising administering a therapeutically effective amount of a Wnt/β-catenin signaling inhibitor, wherein said Wnt/β-catenin signalling inhibitor is IWP-O1, IWP-2, IWP-L6, LGK-974, WIK14, Wnt-C59, IWR-1-endo, Silibinin KYA1797K, Foxy-5, ETC-1922159, Carnosic acid, Pyrvinium, iCRT-14, Sulindac, SM04755, Famotidine, E7449, Dvl-PDZ Domain Inhibitor II, Niraparib, PJ34 HCl, Capmatinib, Curcumin, Genistein, triptolide, Wogonin, Ant1.4Br/Ant1.4Cl, Ipafricept, APCDD1, FzM1, Fz7-21, OTSA101, OTSA101-DTPA-90Y, BNC101, Gigantol, salinomycin, IGFBP-4, DKN-01, Compound 3289-8625, FJ9, NSC668036, peptide Pen-N3, 2X-121, AZ1366, AZ-6102, G007-LK, G244-LM, IWR-1, JW55, JW67, JW74, K-756, MN-64, MSC2504877, NVP-TNKS656, RK-287107, TC-E5001, WIKI4, XAV939, TCS 183, 21H7, isoquercitrin, KY1220, MSAB, NRX-252114, BC21, BC2059, CCT031374, CCT036477, CGP049090, CWP232228, ethacrynic acid, FH535, iCRT3, iCRT5, iCRT14, LF3, NLS-StAx-h, PKF115-584, PKF118-310, PKF118-744, PNU-74654, quercetin, ZTM000990, KY-05009, NCB-0846, IQ-1, windorphen, YH249/250, C-82, ICG-001, PRI-724, retinoids, vitamin D3, SAH-BCL9, lorecivivint, artesunate, cardamonin, cardionogen, CCT031374, diethyl benzylphosphonate, echinacoside, KY02111, pamidronic acid, or specnuezhenide.

2. The method of claim 1, further comprising administering Molnupiravir or Remdesivir to said subject.

3. The method of claim 1, wherein said subject is a human.

4. A method of treating a subject infected with SARS-CoV-2, suspected of being infected with SARS-CoV-2, or at risk of being infected with SARS-CoV-2, comprising administering a therapeutically effective amount of a compound or composition that increases the density of peroxisomes in a plurality of cells in the subject, wherein said compound or composition that increases the density of peroxisomes in a plurality of cells in the subject is Pyrvinium, KYA1797K, Wnt-C59, ETC-1922159, iCRT-14, SM04755, E7449, IWP-01, NCB0846, LGK-974, Triptolide, PJ354 HCL, Wogonin, Ant1.4Br/Ant1.4Cl, Ipafricept, APCDD1, FzM1, Fz7-21, OTSA101, OTSA101-DTPA-90Y, BNC101, Gigantol, salinomycin, IGFBP-4, DKN-01, Compound 3289-8625, FJ9, NSC668036, peptide Pen-N3, 2X-121, AZ1366, AZ-6102, G007-LK, G244-LM, IWR-1, JW55, JW67, JW74, K-756, MN-64, MSC2504877, NVP-TNKS656, RK-287107, TC-E5001, WIKI4, XAV939, TCS 183, 21H7, isoquercitrin, KY1220, MSAB, NRX-252114, BC21, BC2059, CCT031374, CCT036477, CGP049090, CWP232228, ethacrynic acid, FH535, iCRT3, iCRT5, iCRT14, LF3, NLS-StAx-h, PKF115-584, PKF118-310, PKF118-744, PNU-74654, quercetin, ZTM000990, KY-05009, NCB-0846, IQ-1, windorphen, YH249/250, C-82, ICG-001, PRI-724, retinoids, vitamin D3, SAH-BCL9, lorecivivint, artesunate, cardamonin, cardionogen, CCT031374, diethyl benzylphosphonate, echinacoside, KY02111, pamidronic acid, or specnuezhenide.

5. A method of treating a subject infected with SARS-CoV-2, suspected of being infected with SARS-CoV-2, or at risk of being infected with SARS-CoV-2, comprising administering a therapeutically effective amount of a compound or composition that increases the density of peroxisomes in a plurality of cells in the subject, wherein said compound or composition that increases the density of peroxisomes in a plurality of cells in the subject is a PPAR alpha agonist or a PPAR gamma agonist.

6. The method of claim 5, wherein said PPAR alpha agonist is Fenofibrate, ciprofibrate, clofibrate, gemfibrozil, bezafibrate, or Elafibranor.

7. The method of claim 5, wherein said PPAR gamma agonist is Rosiglitazone Maleate, Pioglitazone hydrochloride, Lobeglitazone, chiglitazar, KDT-501, Navaglitazar, AVE-0897, ZY-H2, AMG-131, Muraglitazar, Amorfrutins, Formonetin, Bixin, Norbixin, Commipheric acid, Citral, Meranzin, Carnosic acid, Carnosol, Linoleic acid, Saurufuran, Isosilybin A, Gallotannins, or Carvacrol.

8. The method of claim 4, further comprising administering Molnupiravir or Remdesivir to said subject.

9. The method of claim 4, wherein said subject is a human.

10. The method of claim 5, further comprising administering Molnupiravir or Remdesivir to said subject.

11. The method of claim 5, wherein said subject is a human.

* * * * *